(12) United States Patent
Sheppard et al.

(10) Patent No.: US 7,183,391 B2
(45) Date of Patent: Feb. 27, 2007

(54) KUNITZ DOMAIN POLYPEPTIDE ZKUN10

(75) Inventors: Paul O. Sheppard, Granite Falls, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 11/082,148

(22) Filed: Mar. 16, 2005

(65) Prior Publication Data

US 2005/0176105 A1   Aug. 11, 2005

Related U.S. Application Data

(60) Division of application No. 10/315,432, filed on Dec. 9, 2002, now Pat. No. 6,914,135, which is a continuation of application No. 09/750,964, filed on Dec. 28, 2000, now abandoned.

(60) Provisional application No. 60/173,425, filed on Dec. 29, 1999.

(51) Int. Cl.
*C07K 14/81* (2006.01)
*C12Q 1/25* (2006.01)

(52) U.S. Cl. .................. 530/390.5; 530/350; 530/407; 435/18

(58) Field of Classification Search .............. 530/300, 530/350, 407, 390.5; 435/18
See application file for complete search history.

(56) References Cited

U.S. PATENT DOCUMENTS 6,544,760 B2 * 4/2003 Holloway .................. 435/69.2

OTHER PUBLICATIONS

Sinha et al. (1991) Conversion of the Alzheimer's beta-amyloid precursor protein (APP) Kunitz domain into a potent human neutrophil elastase inhibitor. J. Biol. Chem. vol. 266, No. 31, pp. 21011-21013.*

INC5272550, LIFESEQ™ Clone Information Results, Incyte Pharmaceuticals, Inc., 1999.
INC2763021, LIFESEQ™ Clone Information Results, Incyte Pharmaceuticals, Inc., 1999.
P15989, Doliana et al., 1990.
AAR81918, Ladner et al., 1996.
AA846371, Strausberg, 1998.
AQ141660, Mahairas et al., 1998.
Mayer et al., *European Journal of Biochemistry* 225: 573-580, 1994.
Bonaldo et al., J. Biol. Chem. 264: 20235-20239, 1989.
Ngo et al., "Computational complexity protein structure prediction, and the levinthal paradox," *The Protein Folding Problem and Tertiary Structure Prediction* pp. 491-495, Merz, Jr. K. et al. Eds. Birkhauser, Boston, 1994.
Qin et al., "Functional characterization of Kunitz domains in hepatocyte growth factor activator inhibitor type 2," *FEBS Letters* 436:111-114, 1998.
Doerks et al., "Protein annotation: detective work for function prediction," *TIG* 14:248-250, 1998.

* cited by examiner

*Primary Examiner*—Karen Cochrane Carlson
*Assistant Examiner*—Samuel W. Liu
(74) *Attorney, Agent, or Firm*—Deborah A. Sawislak

(57) ABSTRACT

We claim the proteinase inhibitors comprising a Kunitz domain, wherein the Kunitz domain comprises amino acid residues 57–107 of SEQ ID NO: 2. We also claim a fusion protein comprising said Kunitz domain. In addition, we claim a method of inhibiting protease degradation or protease activity in a composition which contains plasma proteins and proteases. The proteinase inhibitors is used as components of cell culture media in cell culture process, and as inhibitors of protease-mediated degradation of plasma proteins in protein purification.

11 Claims, 2 Drawing Sheets

SEQUENCE LISTING

```
<160> NUMBER OF SEQ ID NOS: 6

<210> SEQ ID NO 1
<211> LENGTH: 836
<212> TYPE: DNA
<213> ORGANISM: Homo sapiens
<220> FEATURE:
<221> NAME/KEY: CDS
<222> LOCATION: (1)...(333)

<400> SEQUENCE: 1 att ttt cta gaa gag aag aga aaa gac atc aca aca tct ata act cag      48
Ile Phe Leu Glu Glu Lys Arg Lys Asp Ile Thr Thr Ser Ile Thr Gln
1               5                   10                  15 caa gaa gca ctt gaa aat tat gaa aat aac aaa tat gac att gaa gaa      96
Gln Glu Ala Leu Glu Asn Tyr Glu Asn Asn Lys Tyr Asp Ile Glu Glu
            20                  25                  30 aat gaa caa gaa aca cca gca aaa caa aaa gaa act aga aaa gaa ata     144
```

```
Asn Glu Gln Glu Thr Pro Ala Lys Gln Lys Glu Thr Arg Lys Glu Ile
            35                  40                  45 aat gca gac act acc tat ggt cct tgt tcc atg gat cca atg gaa ggc      192
Asn Ala Asp Thr Thr Tyr Gly Pro Cys Ser Met Asp Pro Met Glu Gly
 50                  55                  60 gag tgt cag gat cac acc ctg aag tgg cat tac aac aag gag gaa cgg      240
Glu Cys Gln Asp His Thr Leu Lys Trp His Tyr Asn Lys Glu Glu Arg
 65                  70                  75                  80 gtt tgc cag cag ttc tgg tgt ggc agc tgt ggc ggc aat gcc aac cgg      288
Val Cys Gln Gln Phe Trp Cys Gly Ser Cys Gly Gly Asn Ala Asn Arg
                 85                  90                  95 ttt gaa acc aag gaa gaa tgt gag gct tgg tgt gtc cca ata cag          333
Phe Glu Thr Lys Glu Glu Cys Glu Ala Trp Cys Val Pro Ile Gln
            100                 105                 110 taacagtaca agcagagccc tgttactgtt aaaggcagag cttttaatgc tgatgaaatg    393
gagattacca gggctgaggc aggacctcac agctcagaag tgacagccca ttccaacacc    453
ttggacatca gattcctaaa cgtctgaatg ttttcacgcc aacaaggact tgggccagat    513
gatttgtgac ttgaggactg aattctaata gttaaaaaag taactgaaag atatttaaat    573
gaattagaac ggaatgaaaa ataaacttga acttataata ttatttaaaa atttgggggt    633
gctatgtagc aaaataaaaa tcagtgtaag cagtgagaaa aacctaattc agaaatgaat    693
cgaaacttgg tttgttttt  tcaccaccag agaatagggaa atattagtc aaagagaggg    753 catggaagaa gggacatcta atgtgaacga acttcatact tactacttaa tgtagataaa    813
taaaggcatt ctttattaaa tca                                            836

<210> SEQ ID NO 2
<211> LENGTH: 111
<212> TYPE: PRT
<213> ORGANISM: Homo sapiens

<400> SEQUENCE: 2

Ile Phe Leu Glu Glu Lys Arg Lys Asp Ile Thr Thr Ser Ile Thr Gln
 1               5                  10                  15

Gln Glu Ala Leu Glu Asn Tyr Glu Asn Asn Lys Tyr Asp Ile Glu Glu
            20                  25                  30

Asn Glu Gln Glu Thr Pro Ala Lys Gln Lys Glu Thr Arg Lys Glu Ile
            35                  40                  45

Asn Ala Asp Thr Thr Tyr Gly Pro Cys Ser Met Asp Pro Met Glu Gly
 50                  55                  60

Glu Cys Gln Asp His Thr Leu Lys Trp His Tyr Asn Lys Glu Glu Arg
 65                  70                  75                  80

Val Cys Gln Gln Phe Trp Cys Gly Ser Cys Gly Gly Asn Ala Asn Arg
                 85                  90                  95

Phe Glu Thr Lys Glu Glu Cys Glu Ala Trp Cys Val Pro Ile Gln
            100                 105                 110

<210> SEQ ID NO 3
<211> LENGTH: 333
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(333)
<223> OTHER INFORMATION: n = A,T,C or G

<400> SEQUENCE: 3
```

-continued

```
athttyytng argaraarmg naargayath acnacnwsna thacncarca rgargcnytn     60
garaaytayg araayaayaa rtaygayath gargaraayg arcargarac nccngcnaar    120
caraargara cnmgnaarga rathaaygcn gayacnacnt ayggnccntg ywsnatggay    180
ccnatggarg gngartgyca rgaycayacn ytnaartggc aytayaayaa rgargarmgn    240
gtntgycarc arttytggtg yggnwsntgy ggnggnaayg cnaaymgntt ygaracnaar    300
gargartgyg argcntggtg ygtnccnath car                                 333

<210> SEQ ID NO 4
<211> LENGTH: 51
<212> TYPE: PRT
<213> ORGANISM: Artificial Sequence
<220> FEATURE:
<223> OTHER INFORMATION: kunitz motif
<221> NAME/KEY: VARIANT
<222> LOCATION: (2)...(2)
<223> OTHER INFORMATION: Xaa is any residue except Asp, Cys, Gly, His,
      Met,
<220> FEATURE:
<221> NAME/KEY: VARIANT
<222> LOCATION: (3)...(3)
<223> OTHER INFORMATION: Pro or Trp
<223> OTHER INFORMATION: Xaa is Leu, Glu, Met, Gln, Phe, Ser, Thr, Ala
      or
<220> FEATURE:
<221> NAME/KEY: VARIANT
<222> LOCATION: (4)...(4)
<223> OTHER INFORMATION: Pro
<220> FEATURE:
<221> NAME/KEY: VARIANT
<222> LOCATION: (5)...(5)
<223> OTHER INFORMATION: Xaa is any residue except Arg, Cys, Met, Phe,
      Trp, Tyr or Val
<220> FEATURE:
<221> NAME/KEY: VARIANT
<222> LOCATION: (6)...(6)
<223> OTHER INFORMATION: Xaa is any residue except Asn, Cys, Gln, Gly,
      Phe, Ser, Thr or Trp
<220> FEATURE:
<221> NAME/KEY: VARIANT
<222> LOCATION: (7)...(7)
<223> OTHER INFORMATION: Xaa is Arg, Glu, Asn, Ala, Val, Asp, Lys, Ser,
      Tyr or Met
<220> FEATURE:
<221> NAME/KEY: VARIANT
<222> LOCATION: (8)...(8)
<223> OTHER INFORMATION: Xaa is any residue except Asn, Cys, Gly, His,
      Leu, Met, Phe or Trp
<220> FEATURE:
<221> NAME/KEY: VARIANT
<222> LOCATION: (9)...(9)
<223> OTHER INFORMATION: Xaa is Gly or Glu
<223> OTHER INFORMATION: Xaa is Pro, Arg, Leu, Val, Ser, Asp, Ile, Asn
      or
<220> FEATURE:
<221> NAME/KEY: VARIANT
<222> LOCATION: (11)...(11)
<223> OTHER INFORMATION: Thr
<220> FEATURE:
<221> NAME/KEY: VARIANT
<222> LOCATION: (12)...(12)
<223> OTHER INFORMATION: Xaa is any residue except Ala, Cys, Glu, His,
      Ile, Pro, Trp or Val
<220> FEATURE:
<221> NAME/KEY: VARIANT
<222> LOCATION: (13)...(13)
<223> OTHER INFORMATION: Xaa is Arg, Lys, Ala, Asp, Gln, Phe, Gly, Glu,
      Thr or Ser
<220> FEATURE:
<221> NAME/KEY: VARIANT
<222> LOCATION: (14)...(14)
<223> OTHER INFORMATION: Xaa is any residue except Asp, Cys, Glu, Pro or
      Thr
```

-continued

```
<220> FEATURE:
<221> NAME/KEY: VARIANT
<222> LOCATION: (15)...(15)
<223> OTHER INFORMATION: Xaa is any residue except Arg, Asn, Cys, Gly,
      His, Ser, Trp or Tyr
<220> FEATURE:
<221> NAME/KEY: VARIANT
<222> LOCATION: (16)...(16)
<223> OTHER INFORMATION: Xaa is any residue except Ala, Asp, Cys, Gly,
      His, Met, Trp or Tyr
<220> FEATURE:
<221> NAME/KEY: VARIANT
<222> LOCATION: (17)...(17)
<223> OTHER INFORMATION: Xaa is Ser, Ala, Arg, Val, Gln, Lys, Leu, Gly
      or Ile
<220> FEATURE:
<221> NAME/KEY: VARIANT
<222> LOCATION: (18)...(18)
<223> OTHER INFORMATION: Xaa is Phe, Tyr, Ile, Trp or Leu
<220> FEATURE:
<221> NAME/KEY: VARIANT
<222> LOCATION: (19)...(19)
<223> OTHER INFORMATION: Xaa is Tyr, His, Phe, Trp, Asn or Ala
<220> FEATURE:
<221> NAME/KEY: VARIANT
<222> LOCATION: (20)...(20)
<223> OTHER INFORMATION: Xaa is Tyr or Phe
<220> FEATURE:
<221> NAME/KEY: VARIANT
<222> LOCATION: (21)...(21)
<223> OTHER INFORMATION: Xaa is Lys, Asn, Ser or Asp
<220> FEATURE:
<221> NAME/KEY: VARIANT
<222> LOCATION: (22)...(22)
<223> OTHER INFORMATION: Xaa is any residue except Asp, Cys, Glu, His or
      Tyr
<220> FEATURE:
<221> NAME/KEY: VARIANT
<222> LOCATION: (23)...(23)
<223> OTHER INFORMATION: Xaa is any residue except Cys, Met, Pro or Trp
<220> FEATURE:
<221> NAME/KEY: VARIANT
<222> LOCATION: (24)...(24)
<223> OTHER INFORMATION: Xaa is Ala, Lys, Ser, Leu, Thr, Ile, Gln, Glu,
      Tyr or Val
<220> FEATURE:
<221> NAME/KEY: VARIANT
<222> LOCATION: (25)...(25)
<223> OTHER INFORMATION: Xaa is Lys, Gln, Asn, His, Gly, Arg or Met
<220> FEATURE:
<221> NAME/KEY: VARIANT
<222> LOCATION: (27)...(27)
<223> OTHER INFORMATION: Xaa is any residue except Asn, Asp, Cys, His,
      Ile, Pro, Trp, Tyr or Val
<220> FEATURE:
<221> NAME/KEY: VARIANT
<222> LOCATION: (28)...(28)
<223> OTHER INFORMATION: Xaa is any residue except Cys, Gly, Phe, Pro,
      Ser or Trp
<220> FEATURE:
<221> NAME/KEY: VARIANT
<222> LOCATION: (29)...(29)
<223> OTHER INFORMATION: Xaa is any residue except Asp, Cys, His, Ile,
      Phe, Trp or Tyr
<220> FEATURE:
<221> NAME/KEY: VARIANT
<222> LOCATION: (30)...(30)
<223> OTHER INFORMATION: Xaa is Phe or Tyr
<220> FEATURE:
<221> NAME/KEY: VARIANT
<222> LOCATION: (31)...(31)
<223> OTHER INFORMATION: Xaa is any residue except Arg, Cys, Gly or Met
<220> FEATURE:
<221> NAME/KEY: VARIANT
<222> LOCATION: (32)...(32)
<223> OTHER INFORMATION: Xaa is Tyr, Trp, Phe or Asp
<220> FEATURE:
<221> NAME/KEY: VARIANT
<222> LOCATION: (33)...(33)
```

```
<223> OTHER INFORMATION: Xaa is Ser, Gly or Thr
<220> FEATURE:
<221> NAME/KEY: VARIANT
<222> LOCATION: (35)...(35)
<223> OTHER INFORMATION: Xaa is Gly or Ile
<220> FEATURE:
<221> NAME/KEY: VARIANT
<222> LOCATION: (36)...(36)
<223> OTHER INFORMATION: Xaa is Gly, Lys, Arg, Pro, Gln, Leu, Glu, Asn
     or Met
<220> FEATURE:
<221> NAME/KEY: VARIANT
<222> LOCATION: (37)...(37)
<223> OTHER INFORMATION: Xaa is Gly, Lys or Ala
<220> FEATURE:
<221> NAME/KEY: VARIANT
<222> LOCATION: (38)...(38)
<223> OTHER INFORMATION: Xaa is Asn, Lys or Ser
<220> FEATURE:
<221> NAME/KEY: VARIANT
<222> LOCATION: (39)...(39)
<223> OTHER INFORMATION: Xaa is any residue except Cys, His, Ile, Phe,
     Pro, Thr, Trp, Tyr or Val
<220> FEATURE:
<221> NAME/KEY: VARIANT
<222> LOCATION: (40)...(40)
<223> OTHER INFORMATION: Xaa is Asn or Tyr
<220> FEATURE:
<221> NAME/KEY: VARIANT
<222> LOCATION: (41)...(41)
<223> OTHER INFORMATION: Xaa is Arg, Asn, Lys, Gln or Val
<220> FEATURE:
<221> NAME/KEY: VARIANT
<222> LOCATION: (42)...(42)
<223> OTHER INFORMATION: Xaa is Phe, Tyr or Asp
<220> FEATURE:
<221> NAME/KEY: VARIANT
<222> LOCATION: (43)...(43)
<223> OTHER INFORMATION: Xaa is any residue except Cys, Gln, Gly, Phe or
     Trp
<220> FEATURE:
<221> NAME/KEY: VARIANT
<222> LOCATION: (44)...(44)
<223> OTHER INFORMATION: Xaa is Thr, Ser, Arg, Lys or Asp
<220> FEATURE:
<221> NAME/KEY: VARIANT
<222> LOCATION: (45)...(45)
<223> OTHER INFORMATION: Xaa is Ile, Leu, Trp, Arg, Lys, Thr, Glu, Ala,
     Gln or Val
<220> FEATURE:
<221> NAME/KEY: VARIANT
<222> LOCATION: (46)...(46)
<223> OTHER INFORMATION: Xaa is Glu, Asp, Ala, His, Met, Val, Gln, Lys,
     Arg or Pro
<220> FEATURE:
<221> NAME/KEY: VARIANT
<222> LOCATION: (48)...(48)
<223> OTHER INFORMATION: Xaa is Glu, Lys, Gln, Asp, Ala, Tyr or Ser
<220> FEATURE:
<221> NAME/KEY: VARIANT
<222> LOCATION: (49)...(49)
<223> OTHER INFORMATION: Xaa is any residue except Ala, Cys, Gly, Phe,
     Pro, Ser, Thr, Trp or Tyr
<220> FEATURE:
<221> NAME/KEY: VARIANT
<222> LOCATION: (50)...(50)
<223> OTHER INFORMATION: Xaa is any residue except Cys, Ile, Leu, Met,
     Phe, Pro, Ser, Tyr or Val
<220> FEATURE:
<223> OTHER INFORMATION: Xaa is Thr, Ala, Val, Ile, Phe, Leu, Met, Lys,
     Tyr or Arg

<400> SEQUENCE: 4

Cys Xaa Xaa Xaa Xaa Xaa Xaa Xaa Cys Xaa Xaa Xaa Xaa Xaa Xaa
 1               5                  10                  15

Xaa Xaa Xaa Xaa Xaa Xaa Xaa Xaa Xaa Cys Xaa Xaa Xaa Xaa Xaa Xaa
             20                  25                  30
```

```
Xaa Cys Xaa Xaa Xaa Xaa Xaa Xaa Xaa Xaa Xaa Xaa Cys Xaa
         35                  40                  45

Xaa Xaa Cys
     50

<210> SEQ ID NO 5
<211> LENGTH: 1747
<212> TYPE: DNA
<213> ORGANISM: Homo sapiens
<220> FEATURE:
<221> NAME/KEY: CDS
<222> LOCATION: (1)...(1248)

<400> SEQUENCE: 5 atg gat gga acc aac aga ttt tac ttg tac gtc tgg gag aca gag cgc      48
Met Asp Gly Thr Asn Arg Phe Tyr Leu Tyr Val Trp Glu Thr Glu Arg
 1               5                  10                  15 cag cag gat gtg gag cac gtg gcc cgc tgt att ctc tgc tat gac aaa      96
Gln Gln Asp Val Glu His Val Ala Arg Cys Ile Leu Cys Tyr Asp Lys
             20                  25                  30 tgc aga cca gac cca gaa tgc ccg gct ggc acg ccg ggg ccc cag gag     144
Cys Arg Pro Asp Pro Glu Cys Pro Ala Gly Thr Pro Gly Pro Gln Glu
         35                  40                  45 gtg gac gtg gac ttg gta ttt gtg gtg gac agc tcc tat gga gtg gat     192
Val Asp Val Asp Leu Val Phe Val Val Asp Ser Ser Tyr Gly Val Asp
     50                  55                  60 gcc gac gtg tac cgc ggg tct ttg agt cta gcg gac gcc gcg cta gaa     240
Ala Asp Val Tyr Arg Gly Ser Leu Ser Leu Ala Asp Ala Ala Leu Glu
 65                  70                  75                  80 gac ctg gag gtg gct gag cag ccg ggc gcg tcc cac cgt ggg gcg cgt     288
Asp Leu Glu Val Ala Glu Gln Pro Gly Ala Ser His Arg Gly Ala Arg
                 85                  90                  95 gtg gcc ctg gtg acg cac acg aca ccc aac ttc tgg ccg ggg ctt cca     336
Val Ala Leu Val Thr His Thr Thr Pro Asn Phe Trp Pro Gly Leu Pro
            100                 105                 110 ctt gac cac cta tgg caa ccg gaa gca gat gca gag aca tgt gcg cga     384
Leu Asp His Leu Trp Gln Pro Glu Ala Asp Ala Glu Thr Cys Ala Arg
        115                 120                 125 ggc ttc agc cgc ccc tta cag gga acc gcc ccc cct ggc cac gcc ctg     432
Gly Phe Ser Arg Pro Leu Gln Gly Thr Ala Pro Pro Gly His Ala Leu
    130                 135                 140 gag tgg acg ctg gag aat gtg ctc ctg gca gcc cct cgg ccg cgg aag     480
Glu Trp Thr Leu Glu Asn Val Leu Leu Ala Ala Pro Arg Pro Arg Lys
145                 150                 155                 160 gca caa gtc ctc ttc gcc atc gtg gcc agc gag aca agt agc tgg gac     528
Ala Gln Val Leu Phe Ala Ile Val Ala Ser Glu Thr Ser Ser Trp Asp
                165                 170                 175 agg gag aag cta tgg act ctg tcc ctg gag gcc aaa tgc aag ggc att     576
Arg Glu Lys Leu Trp Thr Leu Ser Leu Glu Ala Lys Cys Lys Gly Ile
            180                 185                 190 acc ctc ttt gtg ctg gcc ttg ggt ccg ggt gtg ggg acc cat gag cta     624
Thr Leu Phe Val Leu Ala Leu Gly Pro Gly Val Gly Thr His Glu Leu
        195                 200                 205 gcc gag cta gcc gag ctg gtc agt gct ccc tct gag cag cat cta ctg     672
Ala Glu Leu Ala Glu Leu Val Ser Ala Pro Ser Glu Gln His Leu Leu
    210                 215                 220 cgc cta caa ggg gtc tca gag cca gag gtt aac tac gct cag gga ttc     720
Arg Leu Gln Gly Val Ser Glu Pro Glu Val Asn Tyr Ala Gln Gly Phe
225                 230                 235                 240 act cgg gcc ttc ctg aac ctc cta aaa agt ggg aca aac cag tac cca     768
```

```
                Thr Arg Ala Phe Leu Asn Leu Leu Lys Ser Gly Thr Asn Gln Tyr Pro
                                245                 250                 255 ccc cca gag ctc act gaa gaa tgt ggg ggc cta cac cgt ggg gac act        816
Pro Pro Glu Leu Thr Glu Glu Cys Gly Gly Leu His Arg Gly Asp Thr
            260                 265                 270 gtg ctg caa tta gtc aca cct gtc aac agg ttg ccc agg cac cag ttt        864
Val Leu Gln Leu Val Thr Pro Val Asn Arg Leu Pro Arg His Gln Phe
            275                 280                 285 ggt atg tct ggc ttg gct gat gat ttg gaa gca ctt gaa gca aca ggc        912
Gly Met Ser Gly Leu Ala Asp Asp Leu Glu Ala Leu Glu Ala Thr Gly
            290                 295                 300 att ttt cta gaa gag aag aga aaa gac atc aca aca tct ata act cag        960
Ile Phe Leu Glu Glu Lys Arg Lys Asp Ile Thr Thr Ser Ile Thr Gln
305                 310                 315                 320 caa gaa gca ctt gaa aat tat gaa aat aac aaa tat gac att gaa gaa       1008
Gln Glu Ala Leu Glu Asn Tyr Glu Asn Asn Lys Tyr Asp Ile Glu Glu
                325                 330                 335 aat gaa caa gaa aca cca gcc aaa caa aca gca act aga aaa gaa ata       1056
Asn Glu Gln Glu Thr Pro Ala Lys Gln Thr Ala Thr Arg Lys Glu Ile
            340                 345                 350 aat gca gac act acc tat ggt cct tgt tcc atg gat cca atg gaa ggc       1104
Asn Ala Asp Thr Thr Tyr Gly Pro Cys Ser Met Asp Pro Met Glu Gly
            355                 360                 365 gag tgt cag gat cac acc ctg aag tgg cat tac aac aag gag gaa cgg       1152
Glu Cys Gln Asp His Thr Leu Lys Trp His Tyr Asn Lys Glu Glu Arg
            370                 375                 380 gtt tgc cag cag ttc tgg tgt ggc agc tgt ggc ggc aat gcc aac cgg       1200
Val Cys Gln Gln Phe Trp Cys Gly Ser Cys Gly Gly Asn Ala Asn Arg
385                 390                 395                 400 ttt gaa acc aag gaa gaa tgt gag gct tgg tgt gtc cca ata cag taa       1248
Phe Glu Thr Lys Glu Glu Cys Glu Ala Trp Cys Val Pro Ile Gln  *
                405                 410                 415 cagtacaagc agagccctgt tactgttaaa ggcagagctt ttaatgctga tgaaatggag     1308
attaccaggg ctgaggcagg acctcacagc tcagaagtga cagcccattc caacaccttg     1368
gacatcagat tcctaaacgt ctgaatgttt tcacgccaac aaggacttgg gccagatgat     1428
ttgtgacttg aggactgaat tctaatagtt aaaaaagtaa ctgaaagata tttaaatgaa     1488
ttagaacgga atgaaaaata aacttgaact tataatatta ttttaaaatt tgggggtgct     1548
atgtagcaaa ataaaaatca gtgtaagcag tgagaaaaac ctaattcaga aatgaatcga     1608
aacttggttt gttttttttca ccaccagaga ataggggaaat attagtcaaa gagagggcat   1668
ggaagaaggg acatctaatg tgaacgaact tcatacttac tacttaatgt agataaataa     1728
aggcattctt tattaaatc                                                  1747

<210> SEQ ID NO 6
<211> LENGTH: 415
<212> TYPE: PRT
<213> ORGANISM: Homo sapiens

<400> SEQUENCE: 6

Met Asp Gly Thr Asn Arg Phe Tyr Leu Tyr Val Trp Glu Thr Glu Arg
1               5                   10                  15

Gln Gln Asp Val Glu His Val Ala Arg Cys Ile Leu Cys Tyr Asp Lys
                20                  25                  30

Cys Arg Pro Asp Pro Glu Cys Pro Ala Gly Thr Pro Gly Pro Gln Glu
            35                  40                  45

Val Asp Val Asp Leu Val Phe Val Val Asp Ser Ser Tyr Gly Val Asp
```

-continued

```
            50                  55                  60
Ala Asp Val Tyr Arg Gly Ser Leu Ser Leu Ala Asp Ala Ala Leu Glu
 65              70                  75                  80

Asp Leu Glu Val Ala Glu Gln Pro Gly Ala Ser His Arg Gly Ala Arg
             85                  90                  95

Val Ala Leu Val Thr His Thr Thr Pro Asn Phe Trp Pro Gly Leu Pro
             100                 105                 110

Leu Asp His Leu Trp Gln Pro Glu Ala Asp Ala Glu Thr Cys Ala Arg
         115                 120                 125

Gly Phe Ser Arg Pro Leu Gln Gly Thr Ala Pro Pro Gly His Ala Leu
     130                 135                 140

Glu Trp Thr Leu Glu Asn Val Leu Leu Ala Ala Pro Arg Pro Arg Lys
145                 150                 155                 160

Ala Gln Val Leu Phe Ala Ile Val Ala Ser Glu Thr Ser Ser Trp Asp
                165                 170                 175

Arg Glu Lys Leu Trp Thr Leu Ser Leu Glu Ala Lys Cys Lys Gly Ile
             180                 185                 190

Thr Leu Phe Val Leu Ala Leu Gly Pro Gly Val Gly Thr His Glu Leu
             195                 200                 205

Ala Glu Leu Ala Glu Leu Val Ser Ala Pro Ser Glu Gln His Leu Leu
     210                 215                 220

Arg Leu Gln Gly Val Ser Glu Pro Glu Val Asn Tyr Ala Gln Gly Phe
225                 230                 235                 240

Thr Arg Ala Phe Leu Asn Leu Leu Lys Ser Gly Thr Asn Gln Tyr Pro
                245                 250                 255

Pro Pro Glu Leu Thr Glu Glu Cys Gly Gly Leu His Arg Gly Asp Thr
             260                 265                 270

Val Leu Gln Leu Val Thr Pro Val Asn Arg Leu Pro Arg His Gln Phe
             275                 280                 285

Gly Met Ser Gly Leu Ala Asp Asp Leu Glu Ala Leu Glu Ala Thr Gly
     290                 295                 300

Ile Phe Leu Glu Glu Lys Arg Lys Asp Ile Thr Thr Ser Ile Thr Gln
305                 310                 315                 320

Gln Glu Ala Leu Glu Asn Tyr Glu Asn Asn Lys Tyr Asp Ile Glu Glu
                325                 330                 335

Asn Glu Gln Glu Thr Pro Ala Lys Gln Thr Ala Thr Arg Lys Glu Ile
             340                 345                 350

Asn Ala Asp Thr Thr Tyr Gly Pro Cys Ser Met Asp Pro Met Glu Gly
             355                 360                 365

Glu Cys Gln Asp His Thr Leu Lys Trp His Tyr Asn Lys Glu Glu Arg
     370                 375                 380

Val Cys Gln Gln Phe Trp Cys Gly Ser Cys Gly Gly Asn Ala Asn Arg
385                 390                 395                 400

Phe Glu Thr Lys Glu Glu Cys Glu Ala Trp Cys Val Pro Ile Gln
                405                 410                 415
```

KUNITZ DOMAIN POLYPEPTIDE ZKUN10

REFERENCE TO RELATED APPLICATIONS

This application is a divisional of U.S. application Ser. No. 10/315,432, filed on Dec. 9, 2002, issued as U.S. Pat. No. 6,914,135. which is a continuation of U.S. application Ser. No. 09/750,964 filed Dec. 28, 2000, now abandoned, which is related to U.S. Provisional Application 60/173,425, filed on Dec. 29, 1999, for which claims of benefit are made under 35 U.S.C. § 120 and 35 U.S.C. § 119(e)(1), and is incorporated herein by reference.

BACKGROUND OF THE INVENTION

In animals, proteinases are important in wound healing, extracellular matrix destruction, tissue reorganization, and in cascades leading to blood coagulation, fibrinolysis, and complement activation. Proteinases are released by inflammatory cells for destruction of pathogens or foreign materials, and by normal and cancerous cells as they move through their surroundings.

The activity of proteinases is regulated by inhibitors; 10% of the proteins in blood serum are proteinase inhibitors (Roberts et al., *Critical Reviews in Eukaryotic Gene Expression* 5:385–436, 1995). One family of proteinase inhibitors, the Kunitz inhibitors, includes inhibitors of trypsin, chymotrypsin, elastase, kallikrein, plasmin, coagulation factors XIa and IXa, and cathepsin G. These inhibitors thus regulate a variety of physiological processes, including blood coagulation, fibrinolysis, and inflammation.

Proteinase inhibitors regulate the proteolytic activity of target proteinases by occupying the active site and thereby preventing occupation by normal substrates. Although proteinase inhibitors fall into several unrelated structural classes, they all possess an exposed loop (variously termed an "inhibitor loop", a "reactive core", a "reactive site", or a "binding loop") which is stabilized by intermolecular interactions between residues flanking the binding loop and the protein core (Bode and Huber, *Eur. J. Biochem.* 204:433–451, 1992). Interaction between inhibitor and enzyme produces a stable complex which disassociates very slowly, releasing either virgin (uncleaved) inhibitor, or a modified inhibitor that is cleaved at the scissile bond of the binding loop.

One class of proteinase inhibitors, the Kunitz inhibitors, are generally basic, low molecular weight proteins comprising one or more inhibitory domains ("Kunitz domains"). The Kunitz domain is a folding domain of approximately 50–60 residues which forms a central anti-parallel beta sheet and a short C-terminal helix. This characteristic domain comprises six cysteine residues that form three disulfide bonds, resulting in a double-loop structure. Between the N-terminal region and the first beta strand resides the active inhibitory binding loop. This binding loop is disulfide bonded through the P2 Cys residue to the hairpin loop formed between the last two beta strands. Isolated Kunitz domains from a variety of proteinase inhibitors have been shown to have inhibitory activity (e.g., Petersen et al., *Eur. J. Biochem.* 125:310–316, 1996; Wagner et al., *Biochem. Biophys. Res. Comm.* 186: 1138–1145, 1992; Dennis et al., *J. Biol. Chem.* 270:25411–25417, 1995).

Proteinase inhibitors comprising one or more Kunitz domains include tissue factor pathway inhibitor (TFPI), tissue factor pathway inhibitor 2 (TFPI-2), amyloid β-protein precursor (AβPP), aprotinin, and placental bikunin. TFPI, an extrinsic pathway inhibitor and a natural anticoagulant, contains three tandemly linked Kunitz inhibitor domains. The amino-terminal Kunitz domain inhibits factor VIIa, plasmin, and cathepsin G; the second domain inhibits factor Xa, trypsin, and chymotrypsin; and the third domain has no known activity (Petersen et al., ibid.). TFPI-2 has been shown to be an inhibitor of the amidolytic and proteolytic activities of human factor VIIa-tissue factor complex, factor XIa, plasma kallikrein, and plasmin (Sprecher et al., *Proc. Natl. Acad. Sci. USA* 91:3353–3357, 1994; Petersen et al., *Biochem.* 35:266–272, 1996). The ability of TFPI-2 to inhibit the factor VIIa-tissue factor complex and its relatively high levels of transcription in umbilical vein endothelial cells, placenta and liver suggests a specialized role for this protein in hemostasis (Sprecher et al., ibid.). Aprotinin (bovine pancreatic trypsin inhibitor) is a broad spectrum Kunitz-type serine proteinase inhibitor that has been shown to prevent activation of the clotting cascade. Aprotinin is a moderate inhibitor of plasma kallikrein and plasmin, and blockage of fibrinolysis and extracorporeal coagulation have been detected in patients given aprotinin during open heart surgery (Davis and Whittington, *Drugs* 49:954–983, 1995; Dietrich et al., *Thorac. Cardiovasc. Surg.* 37:92-98, 1989). Aprotinin has also been used in the treatment of septic shock, adult respiratory distress syndrome, acute pancreatitis, hemorrhagic shock, and other conditions (Westaby, *Ann. Thorac. Surg.* 55:1033–1041, 1993; Wachtfogel et al., *J. Thorac. Cardiovasc. Surg.* 106:1–10, 1993). The clinical utility of aprotinin is believed to arise from its inhibitory activity towards plasma kallikrein or plasmin (Dennis et al., ibid.). Placental bikunin is a serine proteinase inhibitor containing two Kunitz domains (Delaria et al., *J. Biol. Chem.* 272:12209–12214, 1997). Individual Kunitz domains of bikunin have been expressed and shown to be potent inhibitors of trypsin, chymotrypsin, plasmin, factor XIa, and tissue and plasma kallikrein (Delaria et al., ibid.).

Known Kunitz-type inhibitors lack specificity and may have low potency. Lack of specificity can result in undesirable side effects, such as nephrotoxicity that occurs after repeated injections of high doses of aprotinin. These limitations may be overcome by preparing isolated Kunitz domains, which may have fewer side effects than traditional anticoagulants. Hence, there is a need in the art for additional Kunitz-type proteinase inhibitors.

DETAILED DESCRIPTION OF THE INVENTION

Figure 1A:
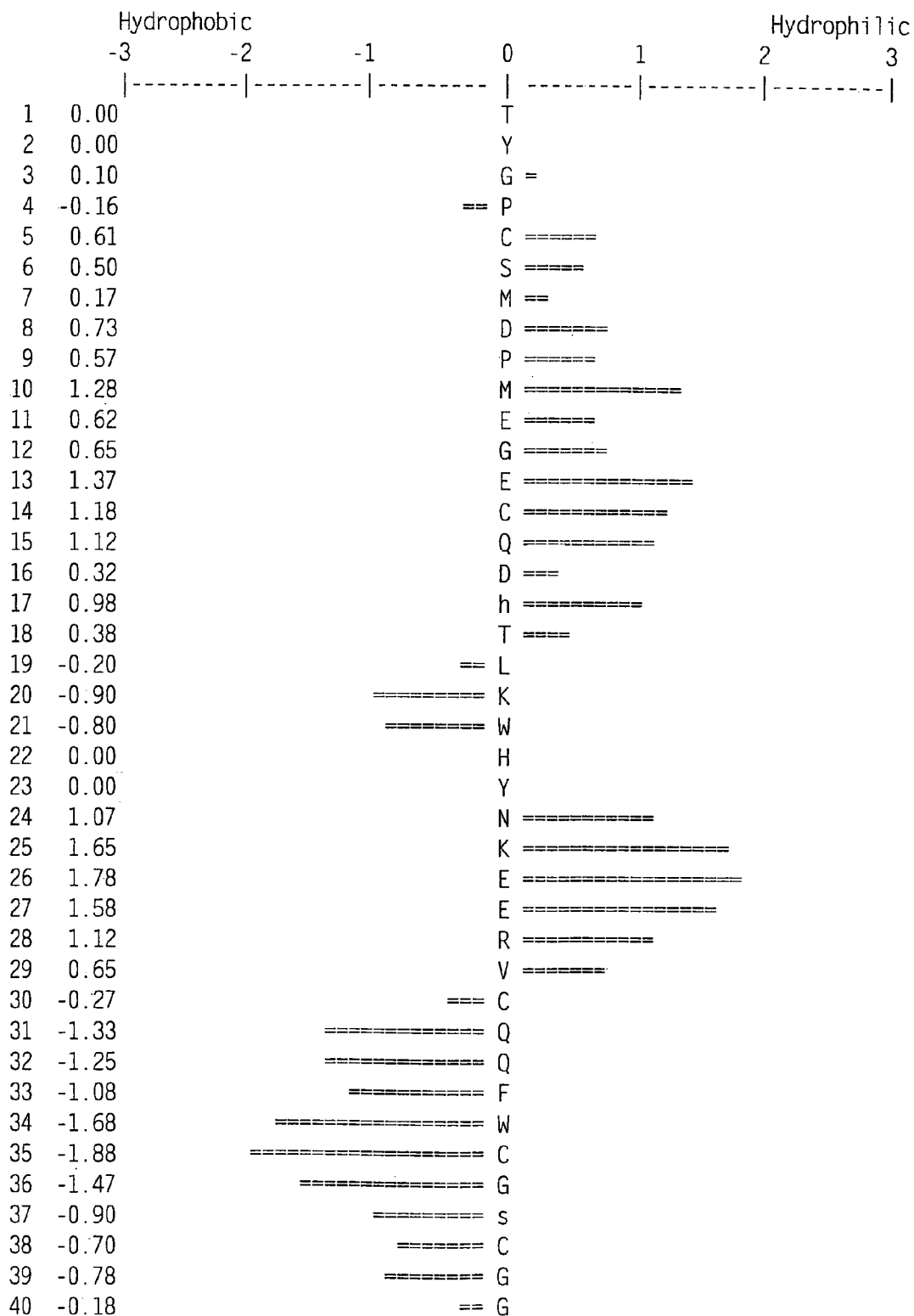
FIGS. 1A and 1B show a Hopp/Woods hydrophilicity profile of the zkun10 protein sequence shown in SEQ ID NO:2. The profile is based on a sliding six-residue window. Buried G, S, and T residues and exposed H, Y, and W residues were ignored. These residues are indicated in the figure by lower case letters.
Figure 1B:
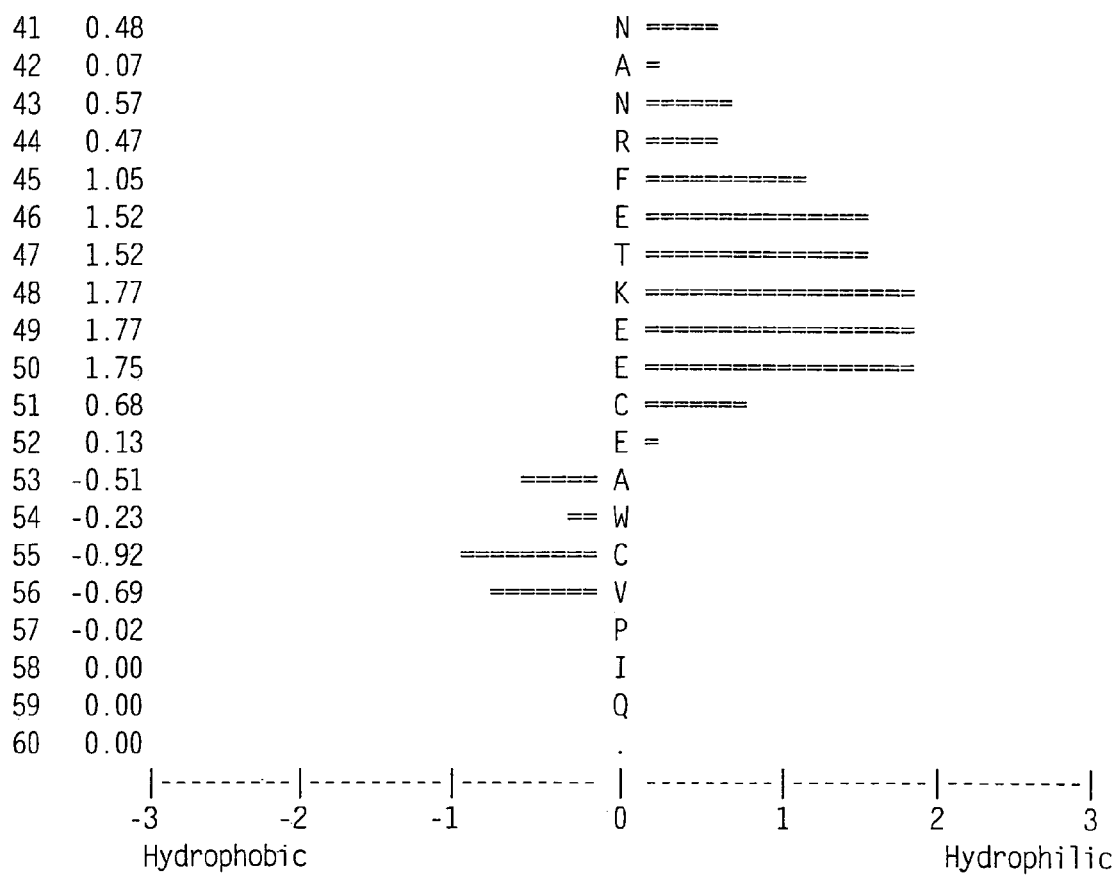

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-hislidine truct, protein A (Nilsson et al., *EMBO J.*

4:1075, 1985; Nilsson et. al., *Methods Enzymol.* 198:3, 1991), glutathione S transferase (Smith and Johnson Gene 67:31, 1988), Glu-Glu affinity tag (Grussenmeyer et al., *Proc. Natl. Acad. Sci. USA* 82:7952–4, 1985), substance P. Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides, in part, novel serine proteinases comprising a Kunitz domain. This Kunitz domain, including sequence variants thereof and proteins containing it, is referred to herein as "zkun10". The zkun10 polypeptide sequence shown in SEQ ID NO:2 comprises this Kunitz domain, which is bounded at the amino and carboxyl termini by cysteine residues at positions 57 and 107, respectively.

Zkun10 has been found to contain at least six exons, with the kunitz domain encoded by nucleotide 1081 to 1233 of SEQ ID NO: 5. The structure as shown in SEQ ID NO: 6 describes a genomic sequence wherein exon 1 comprises nucleotides 1–91; exon 2 comprises nucleotides 92–328; exon 3 comprises nucleotides 329–751; exon 4 comprises nucleotides 752–845; exon 5 comprises nucleotides 846–1075; and exon 6 comprises nucleotides 1076–1747. The entire kunitz domain resides within exon 6, and is represented in SEQ ID NO: 5 from nucleotide 1081 to 1233.

While the sequence begins with a Met (at residue 1 of SEQ ID NO: 6) it is likely that there is additional sequence at the N-terminus of the polypeptide that comprises a signal sequence. The von Willebrand factor domain is shown in SEQ ID NO: 6 as amino acid residues 52 (Asp) to 211 (Leu), and the Kunitz domain is shown as amino acid residues 361 (Cys) to 411 (Cys).

Human alpha 3 type VI collagen is a complex protein that comprises from N-terminus to C-terminus, six von Willebrand domains, a fibronectin III domain and a single kunitz domain. Human alpha 3 type VI collagen also includes globular domains, which with alpha 1 and alpha 2 chains assemble to form collagen type VI (Lamande et al., *J. Biol. Chem.* 273:7423–7430, 1998.) The monomer polypeptides form dimeric, and then tetrameric proteins, which finally result in the formation of microfibrils. Human alpha 3 type VI collagen is found in the subendothelium where it associated with von Willebrand factor and may possibly serve as anchor for interconnecting collagen fibers (Kehrel, *Seminars in Thrombosis and Hemostasis*, 21:123–129, 1995.)

zkun10 has approximately 27% homology with the von Willebrand domain of human alpha 3 type VI collagen. The von Willebrand domain is N-terminal to the kunitz domain. Von Willebrand factor is a large plasma glycoprotein, which plays essential roles in hemostasis (see, for example, Ruggeri, *J. Clin. Invest.* 99:559 (1997)). The von Willebrand factor precursor includes 13 domains that are multiples of domains A to D. The A domains mediate key macromolecular interactions by von Willebrand factor, and A domain mutations are associated with bleeding disorders.

The von Willebrand factor type A domain is a characteristic of a protein superfamily, and occurs in complement factors, integrins, collagen, and other extracellular proteins (see, for example, Colombatti et al., *Matrix* 13:297 (1993), and Bork and Rhode, *Biochem. J.* 279:908 (1991)). Proteins comprising these type A domains participate in a wide variety of biological processes, including cell adhesion, cell migration, and signal transduction (Jenkins et al., *Blood* 91:2032 (1998)). Certain proteins that contain one or more copies of the type A domain take part in host defense mechanisms, such as immune response and inflammation (see, for example, Celikel et al., *Nature Structural Biology* 5:189 (1998)).

Zkun10 has 51% residue identity with the 51-residue kunitz domain in human alpha 3 type VI collagen. The structure of the latter domain has been solved by X-ray crystallography and by NMR (Arnoux et al., *J. Mol. Biol.* 246:609–617, 1995; Sorensen et al., *Biochemistry* 36:10439–10450, 1997). An alignment of zkun10 and the collagen Kunitz domain can be combined with a homology model of zkun10 based on the X-ray structure to predict the function of certain residues in zkun10. Referring to SEQ ID NO:2, disulfide bonds are predicted to be formed by paired cysteine residues Cys57-Cys107; Cys66-Cys90; and Cys82-Cys103. An unpaired Cysteine is found at residue 87, and is buried in the hydrophobic coil of the molecule. While a similar cysteine conformation is not unusual in some proteins, e.g. the fibroblast growth family proteins, it is not common to the kunitz protein family. Therefore, the residue at Cys87 of SEQ ID NO: 2, may be substituted as defined by the limitations of corresponding residue 31 of SEQ ID NO: 4. The protease binding loop (P3-P4') is expected to comprise residues 65–71 of SEQ ID NO:2 (Glu-Cys-Gln-Asp-His-Thr-Leu), with the P1 residue being Gln67, and the P1' residue being Asp68.

Amino acid substitutions can be made within the zkun10 sequence so long as the conserved cysteine residues are retained and the higher order structure is not disrupted. It is preferred to make substitutions within the zkun10 Kunitz domain by reference to the sequences of other Kunitz domains. SEQ ID NO:4 is a generalized Kunitz domain sequence that shows allowable amino acid substitutions based on such an alignment. However, mutants can be made that would purposely alter binding specificity and inhibition profiles. The 51-residue sequence shown in SEQ ID NO:4 conforms to the pattern:

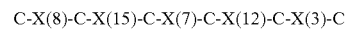

C-X(8)-C-X(15)-C-X(7)-C-X(12)-C-X(3)-C wherein C denotes cysteine; X is any naturally occurring amino acid residue, subject to the limitations set forth in the attached Sequence Listing for SEQ ID NO:4; and the numerals indicate the number of such variable residues. The second cysteine residue is in the P2 position.

Within the present invention up to 20% of the amino acid residues in the zkun10 Kunitz domain (residues 57 through 107 of SEQ ID NO:2) can be replaced with other amino acid residues, subject to the limitation that the resulting substituted sequence is one of the sequences disclosed in SEQ ID NO:4. The present invention thus provides a family of proteins comprising a sequence of amino acid residues as shown in SEQ ID NO:4, wherein the sequence is at least 80% identical to residues 57 through 107 of SEQ ID NO:2. In other embodiments of the present invention, the proteins of the present invention comprise such a sequence that is at least 85%, at least 90%, and at least 95%, 96%, 97%, 98%, or 99% identical to residues 57 through 107 of SEQ ID NO:2.

In other embodiments, the present invention comprises the entire sequence as shown in SEQ ID NOS: 5 and 6. The Kunitz domain resides within this sequence as well (amino acid residues 361–411 of SEQ ID NO: 6), and therefore, substitutions will be limited within that domain to those described above, and shown in the respective locations of SEQ ID NO: 4. With regards to the larger collagen type polypeptides and proteins, certain embodiments of the present invention, the polypeptides and proteins of the present invention comprise such a sequence that is at least 85%, at least 90%, and at least 95%, 96%, 97%, 98%, or 99% identical to SEQ ID NO:6, with the limitations shown in SEQ ID NO: 4 for corresponding regions.

Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

The level of identity between amino acid sequences can be determined using the "FASTA" similarity search algorithm disclosed by Pearson and Lipman (*Proc. Natl. Acad. Sci. USA* 85:2444, 1988) and by Pearson (*Meth. Enzymol.* 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid,

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 | thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus* oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Amino acid sequence changes described herein are made in zkun10 polypeptides so as to minimize disruption of higher order structure essential to biological activity. Amino acid residues that, are critical to maintaining structural integrity can be determined. As shown in SEQ ID NO: 4 specific residues that will be more or less tolerant of change and maintain the overall tertiary structure of the molecule have been described. Methods for analyzing sequence structure include, but are not limited to, alignment of multiple sequences with high amino acid or nucleotide identity, secondary structure propensities, binary patterns, complementary packing, and buried polar interactions (Barton, *Current Opin. Struct. Biol.* 5:372–376, 1995 and Cordes et al., *Current Opin. Struct. Biol.* 6:3–10, 1996). In general, determination of structure will be accompanied by evaluation of activity of modified molecules. For example, changes in amino acid residues will be made so as not to disrupt the protease binding loop structure of the protein family. The effects of amino acid sequence changes can be predicted by, for example, computer modeling using available software (e.g., the Insight II® viewer and homology modeling tools; MSI, San Diego, Calif.) or determined by analysis of crystal structure (see, e.g., Lapthorn et al, *Nature* 369:455–461, 1994; Lapthorn et al., *Nat. Struct. Biol.* 2:266–268, 1995). Protein folding can be measured by circular dichroism (CD). Measuring and comparing the CD spectra generated by a modified molecule and standard molecule are routine in the art (Johnson, *Proteins* 7:205–214, 1990). Crystallography is another well known and accepted method for analyzing folding and structure. Nuclear magnetic resonance (NMR), digestive peptide mapping and epitope mapping are other known methods for analyzing folding and structural similarities between proteins and polypeptides (Schaanan et al., *Science* 257:961–964, 1992). Mass spectrometry and chemical modification using reduction and alkylation can be used to identify cysteine residues that are associated with disulfide bonds or are free of such associations (Bean et al., *Anal. Biochem.* 201:216–226, 1992; Gray, *Protein Sci.* 2:1732–1748, 1993; and Patterson et al., *Anal. Chem.* 66:3727–3732, 1994). Alterations in disulfide bonding will be expected to affect protein folding. These techniques can be employed individually or in combination to analyze and compare the structural features that affect folding of a variant protein or polypeptide to a standard molecule to determine whether such modifications would be significant.

Essential amino acids in the polypeptides of the present invention can be identified experimentally according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88: 4498–4502, 1991). In the latter technique, single alanine mutations are introduced at every residue in the molecule, and the resultant mutant molecules are tested for biological activity as disclosed below to identify amino acid residues that are critical to the activity of the molecule.

Multiple amino acid substitutions can be made and tested using known methods of mutagenesis and screening, such as those disclosed by Reidhaar-Olson and Sauer (*Science* 241: 53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Variants of the disclosed zkun10 DNA and polypeptide sequences can be generated through DNA shuffling as disclosed by Stemmer, *Nature* 370:389–391, 1994 and Stemmer, *Proc. Natl. Acad. Sci. USA* 91:10747–10751, 1994. Briefly, variant genes are generated by in vitro homologous recombination by random fragmentation of a parent gene followed by reassembly using PCR, resulting in randomly introduced point mutations. This technique can be modified by using a family of parent genes, such as allelic variants or genes from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

In many cases, the structure of the final polypeptide product will result from processing of the nascent polypeptide chain by the host cell, thus the final sequence of a zkun10 polypeptide produced by a host cell will not always correspond to the full sequence encoded by the expressed polynucleotide. For example, expressing the complete zkun10 sequence in a cultured mammalian cell is expected to result in removal of at least the secretory peptide, while the same polypeptide produced in a prokaryotic host would not be expected to be cleaved. Differential processing of individual chains may result in heterogeneity of expressed polypeptides.

Additional polypeptides may be joined to the amino and/or carboxyl termini of the zkun10 Kunitz domain (residues 57–107 of SEQ ID NO:2) or a derivative of the zkun10 Kunitz domain as disclosed above. Amino and carboxyl extensions of the zkun10 Kunitz domain will be selected so as not to destroy or mask the proteinase-inhibiting activity of the protein by, for example, burying the Kunitz domain within the interior of the protein. There is a consequent preference for shorter extensions, typically 10–15 residues in length, preferably not exceeding 8 residues in length. There is considerable latitude in the permissible sequence of these extensions, although it is preferred to avoid the addition of cysteine residues in close proximity to the the Kunitz domain itself. For example, a zkun10 protein can comprise residues 57–107 of SEQ ID NO: 2 with amino- and carboxyl-terminal dipeptides, wherein the individual amino acid residues of the dipeptides are any amino acid residue except cysteine. Of particular interest are extensions derived from other members of the Kunitz family proteins and collagen family. The nucleotide sequences and encoded polypeptide domains of the present invention are particularly suited for construction of chimeric molecules comprising a portion of zkun10 and portions from one or more other proteins containing Kunitz domains.

Other amino- and carboxyl-terminal extensions that can be included in the proteins of the present invention include, for example, an amino-terminal methionine residue, a small linker peptide of up to about 20–25 residues, or an affinity tag as disclosed above. A protein comprising such an extension may further comprise a polypeptide linker and/or a proteolytic cleavage site between the zkun10 portion and the affinity tag. Preferred cleavage sites include thrombin cleavage sites and factor Xa cleavage sites. For example, a zkun10 polypeptide of 50 amino acid residues can be expressed as a fusion comprising, from amino terminus to carboxyl terminus: maltose binding protein (approximately 370 residues)—polyhistidine (6 residues)—thrombin cleavage site (Leu-Val-Pro-Arg; SEQ ID NO:5)—zkun10, resulting in a polypeptide of approximately 430 residues. In a second example, a zkun10 polypeptide of 50 residues can be fused to E. coli β-galactosidase (1,021 residues; see Casadaban et al., J. Bacteriol. 143:971–980, 1980), a 10-residue spacer, and a 4-residue factor Xa cleavage site to yield a polypeptide of 1,085 residues. Linker peptides and affinity tags provide for additional functions, such as binding to substrates, antibodies, binding proteins, and the like, and facilitate purification, detection, and delivery of zkun10 proteins. In another example, a zkun10 Kunitz domain can be expressed as a secreted protein comprising a carboxyl-terminal receptor transmembrane domain, permitting the Kunitz domain to be displayed on the surface of a cell. To span the lipid bilayer of the cell membrane, a minimum of about 20 amino acids are required in the transmembrane domain; these should predominantly be hydrophobic amino acids. The Kunitz domain can be separated from the transmembrane domain by a spacer polypeptide, and can be contained within an extended polypeptide comprising a carboxyl-terminal transmembrane domain—spacer polypeptide—Kunitz domain—amino-terminal polypeptide. Many receptor transmembrane domains and polynucleotides encoding them are known in the art. The spacer polypeptide will generally be at least about 50 amino acid residues in length, up to 200–300 or more residues. The amino terminal polypeptide may be up to 300 or more residues in length.

The present invention also provides polypeptide fragments or peptides comprising an epitope-bearing portion of a Zkun10 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., Proc. Nat'l Acad. Sci. USA 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., Science 219: 660 (1983)). Antibodies that recognize short linear epitopes are particularly useful in analytic and diagnostic applications that use denatured protein, such as Western analysis, or in the analysis of fixed cells or tissue samples. Antibodies to linear epitopes are also useful for detecting fragments of Zkun10, such as might occur in body fluids or culture media. Accordingly, antigenic epitope-bearing peptides and polypeptides of the present invention are useful to raise antibodies that bind with the polypeptides described herein.

Antigenic epitope-bearing peptides and polypeptides can contain at least four to ten amino acids, at least ten to fifteen amino acids, or about 15 to about 30 amino acids of SEQ ID NO: 2. Such epitope-bearing peptides and polypeptides can be produced by fragmenting a Zkun10 polypeptide, or by chemical peptide synthesis, as described herein. Moreover, epitopes can be selected by phage display of random peptide libraries (see, for example, Lane and Stephen, Curr. Opin. Immunol. 5:268 (1993), and Cortese et al., Curr. Opin. Biotechnol. 7:616 (1996)). Standard methods for identifying epitopes and producing antibodies from small peptides that comprise an epitope are described, for example, by Mole, "Epitope Mapping," in Methods in Molecular Biology, Vol. 10, Manson (ed.), pages 105–116 (The Humana Press, Inc. 1992), Price, "Production and Characterization of Synthetic Peptide-Derived Antibodies," in Monoclonal Antibodies: Production, Engineering, and Clinical Application, Ritter and Ladyman (eds.), pages 60–84 (Cambridge University Press 1995), and Coligan et al. (eds.), Current Protocols in Immunology, pages 9.3.1–9.3.5 and pages 9.4.1–9.4.11 (John Wiley & Sons 1997).

In particular, fragments of interest include those containing the kunitz domain of amino acid residues 361–411 of SEQ ID NO: 6, and amino acid residues 313–415 which encompasses the kunitz domain and a sequence with similarity to a high affinity binding processing site found in other proteinase inhibitor proteins such as TFPI-2.

The present invention thus provides a series of hybrid molecules in which a segment comprising one or more of the domains of zkun10 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides. The present invention further provides a variety of other polypeptide fusions (and related multimeric proteins comprising one or more polypeptide fusions). For example, a zkun10 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zkun10 polypeptide fusions can be expressed in genetically engineered cells (to produce a variety of multimeric zkun10 analogs). Auxiliary domains can be fused to zkun10 polypeptides to target them to specific cells, tissues, or macromolecules. For example, a zkun10 polypeptide or protein could be targeted to a predetermined cell type by fusing a zkun10 polypeptide to a ligand that specifically binds to a receptor on the surface of that target cell. In this way, polypeptides and proteins can be targeted for therapeutic or diagnostic purposes. A zkun10 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1–9, 1996.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a collagen or Kunitz conferring a biological function may be swapped between zkun10 of the present invention with the functionally equivalent domains from another family member, such as Type 6 collagen, TFPI or TFPI-2. Such components include, but are not limited to, the secretory signal sequence; globular domains, Kunitz domains, helical domains, and von Willebrand domains. Such fusion proteins would be expected to have a biological functional profile that is the same or similar to polypeptides of the present invention or other known serine protease inhibitor family proteins, depending on the fusion constructed. Moreover, such fusion proteins may exhibit other properties as disclosed herein.

Standard molecular biological and cloning techniques can be used to swap the equivalent domains between the zkun10 polypeptide and those polypeptides to which they are fused. Generally, a DNA segment that encodes a domain of interest, e.g., zkun10 Kunitz, or other domains described herein, is operably linked in frame to at least one other DNA segment encoding an additional polypeptide, and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a collagen domain fusion protein containing one or more von Willebrand domains, followed by one or more Kunitz domains. Such fusion proteins can be expressed, isolated, and assayed for activity as described herein.

Also disclosed herein are polynucleotide molecules, including DNA and RNA molecules, encoding zkun10 proteins. These polynucleotides include the sense strand; the anti-sense strand; and the DNA as double-stranded, having both the sense and anti-sense strand annealed together by their respective hydrogen bonds. A representative DNA sequence encoding a zkun10 protein is set forth in SEQ ID NO:1. DNA sequences encoding other zkun10 proteins can be readily generated by those of ordinary skill in the art based on the genetic code. Counterpart RNA sequences can be generated by substitution of U for T. Polynucleotides encoding zkun10 proteins and complementary polynucleotides are useful in the production of zkun10 proteins and for diagnostic and investigatory purposes.

Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zkun10 polypeptide of SEQ ID NO:2. Those skilled in the art will recognize that the degenerate sequence of SEQ ID NO:3 also provides all RNA sequences encoding SEQ ID NO:2 by substituting U for T. Thus, zkun10 polypeptide-encoding polynucleotides comprising nucleotide 158 to nucleotide 333 of SEQ ID NO:3 and their respective RNA equivalents are contemplated by the present invention. Table 2 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |

TABLE 3-continued

| Amino Acid | One Letter Code | Codons | Degenerate Codon |
|---|---|---|---|
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences shown in SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–912, 1980; Haas et al. *Curr. Biol.* 6:315–24, 1996; Wain-Hobson et al., *Gene* 13:355–64, 1981; Grosjean and Fiers, *Gene* 18:199–209, 1982; Holm, *Nuc. Acids Res.* 14:3075–87, 1986; and Ikemura, *J. Mol. Biol.* 158:573–97, 1982. "Preferential codon usage" is a term of art referring to the bias in codon usage within the genomes of certain species, whereby certain protein translation codons are more frequently used, thus favoring one or a few representatives of the possible codons encoding each amino acid (see Table 3). For example, the amino acid threonine (Thr) may be encoded by ACA, ACC, ACG, or ACT, but in mammalian cells ACC is the most commonly used codon. In other species, for example, insect cells, yeast, viruses or bacteria, different Thr codons may be preferred. Preferred codons for a particular species can be introduced into the polynucleotides of the present invention by a variety of methods known in the art. Introduction of preferred codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferred codons can be tested and optimized for expression in various host cell species, and tested for functionality as disclosed herein.

Within certain embodiments of the invention the isolated polynucleotides will hybridize to similar sized regions of SEQ ID NO: 1 or a sequence complementary thereto under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, the isolated polynucleotides of the present invention include DNA and RNA. Methods for preparing DNA and RNA are well known in the art. In general, RNA is isolated from a tissue or cell that produces large amounts of zkun10 RNA. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA (cDNA) is prepared from poly(A)$^+$ RNA using known methods. In the alternative, genomic DNA can be isolated. Polynucleotides encoding zkun10 polypeptides are then identified and isolated by, for example, hybridization or PCR.

Full-length clones encoding zkun10 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zkun10, receptor fragments, or other specific binding partners.

Zkun10 polynucleotide sequences disclosed herein can also be used as probes or primers to clone 5' non-coding regions of a zkun10 gene. Promoter elements from a zkun10 gene can thus be used to direct the expression of heterologous genes in, for example, transgenic animals or patients treated with gene therapy. Cloning of 5' flanking sequences also facilitates production of zkun10 proteins by "gene activation" as disclosed in U.S. Pat. No. 5,641,670. Briefly, expression of an endogenous zkun10 gene in a cell is altered by introducing into the zkun10 locus a DNA construct comprising at least a targeting sequence, a regulatory sequence, an exon, and an unpaired splice donor site. The targeting sequence is a zkun10 5' non-coding sequence that permits homologous recombination of the construct with the endogenous zkun10 locus, whereby the sequences within the construct become operably linked with the endogenous zkun10 coding sequence. In this way, an endogenous zkun10 promoter can be replaced or supplemented with other regulatory sequences to provide enhanced, tissue-specific, or otherwise regulated expression.

Those skilled in the art will recognize that the sequences disclosed in SEQ ID NOS: 1 and 2 represent a single allele of human zkun10. Allelic variants of these sequences can be cloned by probing cDNA or genomic libraries from different individuals according to standard procedures.

The present invention further provides counterpart polypeptides and polynucleotides from other species ("orthologs"). Of particular interest are zkun10 polypeptides from other mammalian species, including murine, porcine, ovine, bovine, canine, feline, equine, and other primate polypeptides. Orthologs of human zkun10 can be cloned using information and compositions provided by the present invention in combination with conventional cloning techniques. For example, a cDNA can be cloned using mRNA obtained from a tissue or cell type that expresses zkun10 as disclosed above. A library is then prepared from mRNA of a positive tissue or cell line. A zkun10-encoding cDNA can then be isolated by a variety of methods, such as by probing with a complete or partial human cDNA or with one or more sets of degenerate probes based on the disclosed sequence. A cDNA can also be cloned using the polymerase chain reaction, or PCR (Mullis, U.S. Pat. No. 4,683,202), using primers designed from the representative human zkun10 sequence disclosed herein. Within an additional method, the cDNA library can be used to transform or transfect host cells, and expression of the cDNA of interest can be detected with an antibody to zkun10 polypeptide. Similar techniques can also be applied to the isolation of genomic clones.

Nucleic acid molecules can be used to detect the expression of a Zkun10 gene in a biological sample. Such probe molecules include double-stranded nucleic acid molecules comprising the nucleotide sequence of SEQ ID NO: 1, or a fragment thereof, as well as single-stranded nucleic acid molecules having the complement of the nucleotide sequence of SEQ ID NO: 1, or a portion thereof. As used herein, the term "portion" refers to at least eight nucleotides to at least 20 or more nucleotides. Probe molecules may be DNA, RNA, oligonucleotides, and the like. Certain probes bind with regions of a Zkun10 gene that have a low sequence similarity to comparable regions in other serine protease inhibitors.

In a basic assay, a single-stranded probe molecule is incubated with RNA, isolated from a biological sample, under conditions of temperature and ionic strength that promote base pairing between the probe and target Zkun10 RNA species.

After separating unbound probe from hybridized molecules, the amount of hybrids is detected.

Well-established hybridization methods of RNA detection include northern analysis and dot/slot blot hybridization (see, for example, Ausubel (1995) at pages 4–1 to 4–27, and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, Zkun10 RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Zkun10 oligonucleotide probes are also useful for in vivo diagnosis. As an illustration, $^{18}F$-labeled oligonucleotides can be administered to a subject and visualized by positron emission tomography (Tavitian et al., *Nature Medicine* 4:467 (1998)).

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

One variation of PCR for diagnostic assays is reverse transcriptase-PCR (RT-PCR). In the RT-PCR technique, RNA is isolated from a biological sample, reverse transcribed to cDNA, and the cDNA is incubated with Zkun10 primers (see, for example, Wu et al. (eds.), "Rapid Isolation of Specific cDNAs or Genes by PCR," in *Methods in Gene Biotechnology*, pages 15–28 (CRC Press, Inc. 1997)). PCR is then performed and the products are analyzed using standard techniques.

As an illustration, RNA is isolated from biological sample using, for example, the guanidinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Zkun10 anti-sense oligomers. Oligo-dT primers offer the advantage that various mRNA nucleotide sequences are amplified that can provide control target sequences. Zkun10 sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Zkun10 probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of Zkun10 expression is cycling probe technology, in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985 (1996), Bekkaoui et al., *Biotechniques* 20:240 (1996)). Alternative methods for detection of Zkun10 sequences can utilize approaches such as nucleic acid sequence-based amplification, cooperative amplification of templates by cross-hybridization, and the ligase chain reaction (see, for example, Marshall et al., U.S. Pat. No. 5,686,272 (1997), Dyer et al., *J. Virol. Methods* 60:161 (1996), Ehricht et al., *Eur. J. Biochem.* 243:358 (1997), and Chadwick et al., *J. Virol. Methods* 70:59 (1998)). Other standard methods are known to those of skill in the art.

Zkun10 probes and primers can also be used to detect and to localize Zkun10 gene expression in tissue samples. Methods for such in situ hybridization are well-known to those of skill in the art (see, for example, Choo (ed.), *In Situ Hybridization Protocols* (Humana Press, Inc. 1994), Wu et al. (eds.), "Analysis of Cellular DNA or Abundance of mRNA by Radioactive In Situ Hybridization (RISH)," in *Methods in Gene Biotechnology*, pages 259–278 (CRC Press, Inc. 1997), and Wu et al. (eds.), "Localization of DNA or Abundance of mRNA by Fluorescence In Situ Hybridization (RISH)," in *Methods in Gene Biotechnology*, pages 279–289 (CRC Press, Inc. 1997)). Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

Zkun10 gene has been localized to 3q21.3 of the human genome. Zkun10 nucleotide sequences can be used in linkage-based testing for various diseases, and to determine whether a subject's chromosomes contain a mutation in the Zkun10 gene. Detectable chromosomal aberrations at the Zkun10 gene locus include, but are not limited to, aneuploidy, gene copy number changes, insertions, deletions, restriction site changes and rearrangements. Of particular interest are genetic alterations that inactivate a Zkun10 gene.

Aberrations associated with a Zkun10 locus can be detected using nucleic acid molecules of the present invention by employing molecular genetic techniques, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83–88 (Humana Press, Inc. 1998)).

The protein truncation test is also useful for detecting the inactivation of a gene in which translation-terminating mutations produce only portions of the encoded protein (see, for example, Stoppa-Lyonnet et al., *Blood* 91:3920 (1998)). According to this approach, RNA is isolated from a biological sample, and used to synthesize cDNA. PCR is then used to amplify the Zkun10 target sequence and to introduce an RNA polymerase promoter, a translation initiation sequence, and an in-frame ATG triplet. PCR products are transcribed using an RNA polymerase, and the transcripts are translated in vitro with a T7-coupled reticulocyte lysate system. The translation products are then fractionated by SDS-PAGE to determine the lengths of the translation products. The protein truncation test is described, for example, by Dracopoli et al. (eds.), *Current Protocols in Human Genetics*, pages 9.11.1–9.11.18 (John Wiley & Sons 1998).

The present invention also contemplates kits for performing a diagnostic assay for Zkun10 gene expression or to analyze the Zkun10 locus of a subject. Such kits comprise nucleic acid probes, such as double-stranded nucleic acid molecules comprising the nucleotide sequence of SEQ ID NOS:1 or 9, or a fragment thereof, as well as single-stranded nucleic acid molecules having the complement of the nucleotide sequence of SEQ ID NOS:1 or 9, or a fragment thereof. Probe molecules may be DNA, RNA, oligonucleotides, and the like. Kits may comprise nucleic acid primers for performing PCR.

Such a kit can contain all the necessary elements to perform a nucleic acid diagnostic assay described above. A kit will comprise at least one container comprising a Zkun10 probe or primer. The kit may also comprise a second container comprising one or more reagents capable of indicating the presence of Zkun10 sequences. Examples of such indicator reagents include detectable labels such as radioactive labels, fluorochromes, chemiluminescent agents, and the like. A kit may also comprise a means for conveying to the user that the Zkun10 probes and primers are used to detect Zkun10 gene expression. For example, written instructions may state that the enclosed nucleic acid molecules can be used to detect either a nucleic acid molecule that encodes Zkun10, or a nucleic acid molecule having a nucleotide sequence that is complementary to a Zkun10-encoding nucleotide sequence, or to analyze chromosomal sequences associated with the Zkun10 locus. The written material can be applied directly to a container, or the written material can be provided in the form of a packaging insert.

Zkun10 proteins, including variants of wild-type zkun10, are tested for activity in protease inhibition assays, a variety of which are known in the art. Preferred assays include those measuring inhibition of trypsin, chymotrypsin, plasmin, cathepsin G, and human leukocyte elastase. See, for example, Petersen et al., *Eur. J. Biochem.* 235:310–316, 1996. In a typical procedure, the inhibitory activity of a test compound is measured by incubating the test compound with the proteinase, then adding an appropriate substrate, typically a chromogenic peptide substrate. See, for example, Norris et al. (*Biol. Chem. Hoppe-Seyler* 371:37–42, 1990). Briefly, various concentrations of the inhibitor are incubated in the presence of trypsin, plasmin, and plasma kallikrein in a low-salt buffer at pH 7.4, 25° C. After 30 minutes, the residual enzymatic activity is measured by the addition of a chromogenic substrate (e.g., S2251 (D-Val-Leu-Lys-Nan) or S2302 (D-Pro-Phe-Arg-Nan), available from Kabi, Stockholm, Sweden) and a 30-minute incubation. Inhibition of enzyme activity is indicated by a decrease in absorbance at 405 nm or fluorescence Em at 460 nm. From the results, the apparent inhibition constant $K_i$ is calculated. The inhibition of coagulation factors (e.g., factor VIIa, factor Xa) can be measured using chromogenic substrates or in conventional coagulation assays (e.g., clotting time of normal human plasma; Dennis et al., ibid.).

Zkun10 proteins can be tested in animal models of disease, particularly tumor models, models of fibrinolysis, and models of imbalance of hemostasis. Suitable models are known in the art. For example, inhibition of tumor metastasis can be assessed in mice into which cancerous cells or tumor tissue have been introduced by implantation or injection (e.g., Brown, *Advan. Enzyme Regul.* 35:293–301, 1995; Conway et al., *Clin. Exp. Metastasis* 14:115–124, 1996). Effects on fibrinolysis can be measured in a rat model wherein the enzyme batroxobin and radiolabeled fibrinogen are administered to test animals. Inhibition of fibrinogen activation by a test compound is seen as a reduction in the circulating level of the label as compared to animals not receiving the test compound. See, Lenfors and Gustafsson, *Semin. Thromb. Hemost.* 22:335–342, 1996. Zkun10 proteins can be delivered to test animals by injection or infusion, or can be produced in vivo by way of, for example, viral or naked DNA delivery systems or transgenic expression.

Exemplary viral delivery systems include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–189, 1994; and Douglas and Curiel, *Science & Medicine* 4:44–53, 1997). The adenovirus system offers several advantages: adenovirus can (i) accommodate relatively large DNA inserts; (ii) be grown to high titer; (iii) infect a broad range of mammalian cell types; and (iv) be used with a large number of available vectors containing different promoters. Also, because adenoviruses are stable in the bloodstream, they can be administered by intravenous injection. By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963-967, 1992; and Johnston and Tang, *Meth. Cell Biol.* 43:353–365, 1994.

Transgenic mice, engineered to express a zkun10 gene, and mice that exhibit a complete absence of zkun10 gene function, referred to as "knockout mice" (Snouwaert et al., *Science* 257:1083, 1992), can also be generated (Lowell et al., *Nature* 366:740–742, 1993). These mice are employed to study the zkun10 gene and the encoded protein in an in vivo system. Transgenic mice are particularly useful for investigating the role of zkun10 proteins in early development because they allow the identification of developmental abnormalities or blocks resulting from the over- or under-expression of a specific factor.

The zkun10 polypeptides of the present invention, including full-length polypeptides, biologically active fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zkun10 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zkun10 polypeptide into the secretory pathway of a host cell, a secretory signal sequence (also known as a leader sequence, prepro sequence or pre sequence) is provided in the expression vector. The secretory signal sequence may be that of zkun10, or may be derived from another secreted protein (e.g., t-PA) or synthesized de novo. The secretory signal sequence is operably linked to the zkun10 DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-KI; ATCC No. CCL 61) cell lines. Additional suitable cell lines are known in the art and available from public depositories such as the American Type Culture Collection, 10801 University Boulevard, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Boulevard, Manassas, Va. under accession numbers 98669 and 98668, respectively.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of

*Agrobacterium rhizogenes* as a vector for expressing genes in plant cells has been reviewed by Sinkar et al., *J. Biosci. (Bangalore)* 11:47–58, 1987. Insect cells can be infected with recombinant baculovirus vectors, which are commonly derived from *Autographa californica* multiple nuclear polyhedrosis virus (AcMNPV). DNA encoding the polypeptide of interest is inserted into the viral genome in place of the polyhedrin gene coding sequence by homologous recombination in cells infected with intact, wild-type AcMNPV and transfected with a transfer vector comprising the cloned gene operably linked to polyhedrin gene promoter, terminator, and flanking sequences. The resulting recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zkun10 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors.

It is preferred to purify the proteins of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zkun10 proteins are purified by conventional protein purification methods, typically by a combination of chromatographic techniques. Polypeptides comprising a polyhistidine affinity tag (typically about 6 histidine residues) are purified by affinity chromatography on a nickel chelate resin. See, for example, Houchuli et al., *Bio/Technol.* 6:1321–1325, 1988.

Using methods known in the art, zkun10 proteins can be produced glycosylated or non-glycosylated; pegylated or non-pegylated; and may or may not include an initial methionine amino acid residue.

The zkun10 proteins are contemplated for use in the treatment or prevention of conditions associated with excessive proteinase activity, in particular an excess of trypsin, plasmin, kallikrein, elastase, cathepsin G, proteinase-3, thrombin, factor VIIa, factor IXa, factor Xa, factor XIa, factor XIIa, or matrix metalloproteinases. Such conditions include, but are not limited to, acute pancreatitis, cardiopulmonary bypass (CPB)-induced pulmonary injury, allergy-induced protease release, deep vein thrombosis, myocardial infarction, shock (including septic shock), hyperfibrinolytic hemorrhage, emphysema, rheumatoid arthritis, adult respiratory distress syndrome, chronic inflammatory bowel disease, psoriasis, and other inflammatory conditions. Zkun10 proteins are also contemplated for use in preservation of platelet function, organ preservation, and wound healing.

Zkun10 proteins may be useful in the treatment of conditions arising from an imbalance in hemostasis, including acquired coagulopathies, primary fibrinolysis and fibrinolysis due to cirrhosis, and complications from high-dose thrombolytic therapy. Acquired coagulopathies can result from liver disease, uremia, acute disseminated intravascular coagulation, post-cardiopulmonary bypass, massive transfusion, or Warfarin overdose (Humphries, *Transfusion Medicine* 1:1181–1201, 1994). A deficiency or dysfunction in any of the procoagulant mechanisms predisposes the patient to either spontaneous hemorrhage or excess blood loss associated with trauma or surgery. Acquired coagulopathies usually involve a combination of deficiencies, such as deficiencies of a plurality of coagulation factors, and/or platelet dysfunction. In addition, patients with liver disease commonly experience increased fibrinolysis due to an inability to maintain normal levels of $\alpha 2$-antiplasmin and/or decreased hepatic clearance of plasminogen activators (Shuman, *Hemorrhagic Disorders*, in Bennet and Plum, eds. *Cecil Textbook of Medicine*, 20th ed., W.B. Saunders Co., 1996). Primary fibrinolysis results from a massive release of plasminogen activator. Conditions associated with primary fibrinolysis include carcinoma of the prostate, acute promyelocytic leukemia, hemangiomas, and sustained release of plasminogen activator by endothelial cells due to injection of venoms. The condition becomes critical when enough plasmin is activated to deplete the circulating level of $\alpha_2$-antiplasmin (Shuman, ibid.). Data suggest that plasmin on endothelial cells may be related to the pathophysiology of bleeding or rethrombosis observed in patients undergoing high-dose thrombolytic therapy for thrombosis. Plasmin may cause further damage to the thrombogenic surface of blood vessels after thrombolysis, which may result in rethrombosis (Okajima, *J. Lab. Clin. Med.* 126:1377–1384, 1995).

Additional antithrombotic uses of zkun10 proteins include treatment or prevention of deep vein thrombosis, pulmonary embolism, post-surgical thrombosis, and regulation of blood pressure.

Zkun10 proteins may also be used within methods for inhibiting blood coagulation in mammals, such as in the treatment of disseminated intravascular coagulation. Zkun10 proteins may thus be used in place of known anticoagulants such as heparin, coumarin, and anti-thrombin III. Such methods will generally include administration of the protein in an amount sufficient to produce a clinically significant inhibition of blood coagulation. Such amounts will vary with the nature of the condition to be treated, but can be predicted on the basis of known assays and experimental animal models, and will in general be within the ranges disclosed below.

Zkun10 proteins may also find therapeutic use in the blockage of proteolytic tissue degradation. Proteolysis of extracellular matrix, connective tissue, and other tissues and organs is an element of many diseases. This tissue destruction is beleived to be initiated when plasmin activates one or more matrix metalloproteinases (e.g., collagenase and metallo-elastases). Inhibition of plasmin by zkun10 proteins may thus be beneficial in the treatment of these conditions.

Matrix metalloproteinases (MMPs) are believed to play a role in metastases of cancers, abdominal aortic aneurysm, multiple sclerosis, rheumatoid arthritis, osteoarthritis, trauma and hemorrhagic shock, and corneal ulcers. MMPs produced by tumor cells break down and remodel tissue matrices during the process of metastatic spread. There is evidence to suggest that MMP inhibitors may block this activity (Brown, *Advan. Enzyme Regul.* 35:293–301, 1995). Abdominal aortic aneurysm is characterized by the degradation of extracellular matrix and loss of structural integrity of the aortic wall. Data suggest that plasmin may be important in the sequence of events leading to this destruction of aortic matrix (Jean-Claude et al., *Surgery* 116:472–478, 1994). Proteolytic enzymes are also believed to contribute to the inflammatory tissue damage of multiple sclerosis (Gijbels, *J. Clin. Invest.* 94:2177-2182, 1994). Rheumatoid arthritis is a chronic, systemic inflammatory disease predominantly affecting joints and other connective tissues, wherein proliferating inflammatory tissue (panus) may cause joint deformities and dysfunction (see, Arnett, in *Cecil Textbook of Medicine*, ibid.). Osteoarthritis is a chronic disease causing deterioration of the joint cartilage and other joint tissues and the formation of new bone (bone spurs) at the margins of the joints. There is evidence that MMPs participate in the degradation of collagen in the matrix of osteoarthritic articular cartilage. Inhition of MMPs results in the inhibition of the removal of collagen from cartilage matrix (Spirito, *Inflam. Res.* 44 (supp. 2):S131–S132, 1995; O'Byrne, *Inflam. Res.* 44 (supp. 2):S117–S118, 1995; Karran, *Ann. Rheumatic Disease* 54:662–669, 1995). Zkun10 proteins may also be useful in the treatment of trauma and hemorrhagic shock. Data suggest that administration of an MMP inhibitor after hemorrhage improves cardiovascular response, hepatocellular function, and microvascular blood flow in various organs (Wang, *Shock* 6:377–382, 1996). Corneal ulcers, which can result in blindness, manifest as a breakdown of the collagenous stromal tissue. Damage due to thermal or chemical injury to corneal surfaces often results in a chronic wound-healing situation. There is direct evidence for the role of MMPs in basement membrane defects associated with failure to re-epithelialize in cornea or skin (Fini, *Am. J. Pathol.* 149:1287–1302, 1996).

The zkun10 proteins of the present invention may be combined with other therapeutic agents to augment the activity (e.g., antithrombotic or anticoagulant activity) of such agents. For example, a zkun10 protein may be used in combination with tissue plasminogen activator in thrombolytic therapy.

Doses of zkun10 proteins will vary according to the severity of the condition being treated and may range from approximately 10 µg/kg to 10 mg/kg body weight, preferably 100 µg/kg to 5 mg/kg, more preferably 100 µg/kg to 1 mg/kg. The proteins formulated in a pharmaceutically acceptable carrier or vehicle. It is preferred to prepare them in a form suitable for injection or infusion, such as by dilution with with sterile water, an isotonic saline or glucose solution, or similar vehicle. In the alternative, the protein may be packaged as a lyophilized powder, optionally in combination with a pre-measured diluent, and resuspended immediately prior to use. Pharmaceutical compositions may further include one or more excipients, preservatives, solubilizers, buffering agents, albumin to prevent protein loss on vial surfaces, etc. Formulation methods are within the level of ordinary skill in the art. See, *Remington: The Science and Practice of Pharmacy*, Gennaro, ed., Mack Publishing Co., Easton, Pa., 19th ed., 1995.

Gene therapy provides an alternative therapeutic approach for delivery of zkun10 proteins. If a mammal has a mutated or absent zkun10 gene, a polynucleotide encoding a zkun10 protein can be introduced into the cells of the mammal. In one embodiment, a gene encoding a zkun10 protein is introduced in vivo in a viral vector. Such vectors include an attenuated or defective DNA virus, such as herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, without limitation, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

Within another embodiment, a zkun10 polynucleotide can be introduced in a retroviral vector, as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO Publication No. WO 95/07358; and Kuo et al., Blood 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988).

Within a further embodiment, target cells are removed from the body, and a vector is introduced into the cells as a naked DNA plasmid. The transformed cells are then re-implanted into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, for example, Wu et al., *J. Biol. Chem.* 267:963–7, 1992; Wu et al., *J. Biol. Chem.* 263:14621–4, 1988.

Zkun10 proteins can also be used to prepare antibodies that specifically bind to zkun10 proteins. As used herein, the term "antibodies" includes polyclonal antibodies, monoclonal antibodies, antigen-binding fragments thereof such as $F(ab')_2$ and Fab fragments, single chain antibodies, and the like, including genetically engineered antibodies. Non-human antibodies can be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Alternative techniques for generating or selecting antibodies useful herein include in vitro exposure of lymphocytes to a zkun10 protein, and selection of antibody display libraries in phage or similar vectors (for instance, through use of immobilized or labeled zkun10 polypeptide). Antibodies are defined to be specifically binding if they bind to a zkun10 protein with an affinity at least 10-fold greater than the binding affinity to control (non-zkun10) polypeptide. It is preferred that the antibodies exhibit a binding affinity $(K_a)$ of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of a monoclonal antibody can be readily determined by one of ordinary skill in the art (see, for example, Scatchard, *Ann. NY Acad. Sci.* 51:660–672, 1949).

Methods for preparing polyclonal and monoclonal antibodies are well known in the art (see for example, Hurrell, J. G. R., Ed., *Monoclonal Hybridoma Antibodies: Techniques and Applications, CRC Press*, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a zkun10 protein may be increased through the use of an adjuvant such as alum (aluminum hydroxide) or Freund's complete or incomplete adjuvant. Polypeptides useful for immunization also include fusion polypeptides, such as fusions of a zkun10 protein or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Immunogenic zkun10 polypeptides may be as small as 5 residues. It is preferred to use polypeptides that are hydrophilic or comprise a hydrophilic region. A preferred such region of SEQ ID NO: 2 includes residues 44 (Asn)-54 (Asp).

A variety of assays known to those skilled in the art can be utilized to detect antibodies that specifically bind to a zkun10 protein. Exemplary assays are described in detail in *Antibodies: A Laboratory Manual*, Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zkun10 may be used for affinity purification of zkun10 proteins; within diagnostic assays for determining circulating levels of zkun10 proteins; for detecting or quantitating soluble zkun10 protein as a marker of underlying pathology or disease; for immunolocalization within whole animals or tissue sections, including immunodiagnostic applications; for immunohistochemistry; for screening expression libraries; and for other uses that will be evident to those skilled in the art. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates.

Zkun10 proteins may be used in the laboratory or commercial preparation of proteins from cultured cells. The proteins can be used alone to inhibit specific proteolysis or can be combined with other proteinase inhibitors to provide a "cocktail" with a broad spectrum of activity. Of particular interest is the inhibition of cellular proteases, which can be release during cell lysis. The proteins can also be used in the laboratory as a tissue culture additive to prevent cell detachment.

Zkun10 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing the Zkun10 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of Zkun10 would be unique unto itself.

The antibodies which bind specifically to Zkun10 can be used as a teaching aid to instruct students how to prepare affinity chromatography columns to purify Zkun10, cloning and sequencing the polynucleotide that encodes an antibody and thus as a practicum for teaching a student how to design humanized antibodies. The Zkun10 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the Zkun10 gene, polypeptide, or antibody are considered within the scope of the present invention.

In summary, the present invention provides isolated polypeptides comprising a sequence of amino acid residues as shown in SEQ ID NO: 2 from residue 57 to residue 107. In other embodiments, the present invention includes polypeptides that have at least 95% identity to SEQ ID NO: 2 from residue 1 to residue 111. Changes with the amino acid sequence of SEQ ID NO: 2 from residue 57 to residue 107, or polynucleotides encoding that sequence, will be subject to the limitations as shown in SEQ ID NO: 4, which is illustrative of a motif for the Kunitz domain. Other embodiments include isolated polypeptides with 95% identity to those shown in SEQ ID NO: 6 from residues 1 to 415, which include a Kunitz domain as shown in residues 361 to 415 (and are subject to the same limitations as described herein for SEQ ID NO: 2 residues 57 to 107).

In another aspect; the present invention includes fusion proteins comprising at least polypeptides, of which at least one polypeptide comprises a sequence of amino acid residues as shown in SEQ ID NO: 2 from residue 57 to residue 107. Other embodiment include fusion proteins of at least three polypeptides, wherein the first polypeptide comprises a secretory signal sequence; the second polypeptide comprises a collagen domain containing one or more von Willebrand domains; and a third polypeptide comprising one or more Kunitz domains, one of which comprises the sequence of amino acid residues as shown in SEQ ID NO: 2 from residue 57 to 107. In additional embodiments, the fusion protein will contain collagen globular domains.

In another aspect, the present invention provides expression vectors comprising a transcription promoter, a DNA segment encoding for polypeptides as described above, and a transcription terminator. In another aspect, the expression vector will expressed in a cultured cell. In another aspect, the present invention includes methods by which the polypeptide expressed by the cultured is recovered. The present invention also provides antibodies which specifically bind the polypeptides described herein.

In other aspects, the present invention provides polynucleotide molecules that encode for the polypeptides described herein. In certain embodiments the polynucleotides comprise a sequence of nucleotides as shown in SEQ ID NO: 1 from nucleotide 169 to nucleotide 321 or as shown in SEQ ID NO: 1 from nucleotide 1 to nucleotide 333; or as shown in SEQ ID NO: 5 from nucleotide 1 to nucleotide 1248.

The present invention also provides methods for inhibiting protease degradation, in particular in compositions that contain plasma proteins. These compositions will have a composition comprising zkun10 polypeptides as described herein added to the protein composition in an amount sufficient to reduce the degradation of the protein composition by proteases. The reduction in protease degradation or activity can be measured using chromogenic assays or clotting assays.

The invention is further illustrated by the following non-limiting examples.

EXAMPLES

Example 1

Cloning Zkun10

To obtain a Zkun10 cDNA clone, cDNA is prepared from stomach using a a commercially available kit (Marathon™ cDNA Amplification Kit from Clontech Laboratories, Inc., Palo Alto, Calif.) and an oligo(dT) primer. To amplify the zkun10 DNA, 5 µl each of 1/100 diluted cDNAs, 20 pmoles each of two oligonucleotide primers designed from SEQ ID NO: 1, and 1 U of a 2:1 mixture of ExTaq™ DNA polymerase (TaKaRa Biomedicals) and Pfu DNA polymerasse (Stratagene, La Jolla, Calif.) (ExTaq/Pfu) are used in a 25-µl reaction mixture. The reaction mixture is incubated at 94° C. for 2 minutes; 25 cycles of 94° C. for 15 seconds, 66° C. for 20 seconds, and 72° C. for 30 seconds; and a 1-minute incubation at 72° C. 1 µl each of 1/100 diluted first PCR product is used as template for a nested PCR. 20 pmoles each of two additional oligonucleotide primers and 1 U of ExTaq/Pfu are used in 25-µl reaction mixtures. The mixtures are incubated at 94° C. for 2 minutes; 2 cycles of 94° C. for 15 seconds, 66° C. for 20 seconds, 72° C. for 30 seconds; 25 cycles of 94° C. for 15 seconds, 64° C. for 20 seconds, 72° C. for 30 seconds; and a 1-minute incubation at 72° C. The PCR products are gel purified and sequenced to confirm their identity.

To construct an expression vector for the zkun10 Kunitz domain, PCR is performed on cDNA prepared from stomach as disclosed above. Primers are designed such that the PCR product will encode an intact Kunitz domain with restriction sites Bam HI in the sense primer and Xho I in the antisense primer to facilitate subcloning into an expression vector. 5 µl of 1/100 diluted cDNA, 20 pmoles of each oligonucleotide primer, and 1 U of ExTaq/Pfu are used in 25-µl reaction mixtures. The mixtures are incubated at 94° C. for 2 minutes; 3 cycles of 94° C. for 30 seconds, 50° C. for 30 seconds, 72° C. for 30 seconds; 35 cycles of 94° C. for 30 seconds, 68° C. for 30 seconds; and a 7-minute incubation at 72° C. The PCR product is gel purified and restriction digested with Bam HI and Xho I overnight.

A mammalian expression vector is constructed with the dihyrofolate reductase gene selectable marker under control of the SV40 early promoter, SV40 polyadenylation site, a cloning site to insert the gene of interest under control of the mouse metallothionein 1 (MT-1) promoter and the hGH polyadenylation site. The expression vector is designated pZP-9 and has been deposited at the American Type Culture Collection, 10801 University Boulevard, Manassas, Va. under accession no 98668. To facilitate protein purification, the pZP9 vector is modified by addition of a tissue plasminogen activator (t-PA) secretory signal sequence (see U.S. Pat. No. 5,641,655) and a GluGlu tag sequence (SEQ ID NO: 6) between the MT-1 promoter and hGH terminator. The t-PA secretory signal sequence replaces the native secretory signal sequence for DNAs encoding polypeptides of interest that are inserted into this vector, and expression results in an N-terminally tagged protein. The N-terminally tagged vector was designated pZP9NEE. The vector pZP-NEE is digested with Bam HI and Xho I, and the zkun10 fragment is inserted. The resulting construct is confirmed by sequencing.

Example 2

Expression of Zkun10 in CHO Cells

CHO DG44 cells (Chasin et al., *Som. Cell. Molec. Genet.* 12:555–666, 1986) are plated in 10-cm tissue culture dishes and allowed to grow to approximately 50% to 70% confluency overnight at 37° C., 5% $CO_2$, in Ham's F12/FBS media (Ham's F12 medium (Life Technologies), 5% fetal bovine serum (Hyclone, Logan, Utah), 1% L-glutamine (JRH Biosciences, Lenexa, Kans.), 1% sodium pyruvate (Life Technologies)). The cells are then transfected with the plasmid zkun10/pZMP6 by liposome-mediated transfection using a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filetered water (Lipofectamine™ Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Zkun10/pZMP6 is diluted into 15-ml tubes to a total final volume of 640 μl with SF media. 35 μl of Lipofectamine™ is mixed with 605 μl of SF medium. The resulting mixture is added to the DNA mixture and allowed to incubate approximately 30 minutes at room temperature. Five ml of SF media is added to the DNA:Lipofectamine™ mixture. The cells are rinsed once with 5 ml of SF media, aspirated, and the DNA:Lipofectamine™ mixture is added. The cells are incubated at 37° C. for five hours, then 6.4 ml of Ham's F12/10% FBS, 1% PSN media is added to each plate. The plates are incubated at 37° C. overnight, and the DNA:Lipofectamine™ mixture is replaced with fresh 5% FBS/Ham's media the next day. On day 3 post-transfection, the cells are split into T-175 flasks in growth medium. On day 7 postransfection, the cells are stained with FITC-anti-CD8 monoclonal antibody (Pharmingen, San Diego, Calif.) followed by anti-FITC-conjugated magnetic beads (Miltenyi Biotec). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 μl per well as necessary during this process. When a large percentage of the colonies in the plate are near confluency, 100 μl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5 mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labelling kit; Amersham Corp., Arlington Heights, Ill.) according to the manufacturer's directions and exposed to film (Hyperfilm ECL, Amersham Corp.) for approximately 5 minutes. Positive clones are trypsinized from the 96-well dish and transferred to 6-well dishes in selection medium for scaleup and analysis by Western blot.

Example 3

Expression of Zkun10 in BHK Cells

Full-length zkun10 protein is produced in BHK cells transfected with pZMP6/zkun10 (Example 1). BHK 570 cells (ATCC CRL-10314) are plated in 10-cm tissue culture dishes and allowed to grow to approximately 50 to 70% confluence overnight at 37° C., 5% $CO_2$, in DMEM/FBS media (DMEM, Gibco/BRL High Glucose; Life Technologies), 5% fetal bovine serum (Hyclone, Logan, Utah), 1 mM L-glutamine (JRH Biosciences, Lenexa, Kans.), 1 mM sodium pyruvate (Life Technologies). The cells are then transfected with pZMP6/zkun10 by liposome-mediated transfection (using Lipofectamine™; Life Technologies), in serum free (SF) media (DMEM supplemented with 10 mg/ml transferrin, 5 mg/ml insulin, 2 mg/ml fetuin, 1% L-glutamine and 1% sodium pyruvate). The plasmid is diluted into 15-ml tubes to a total final volume of 640 μl with SF media. 35 μl of the lipid mixture is mixed with 605 μl of SF medium, and the resulting mixture is allowed to incubate approximately 30 minutes at room temperature. Five milliliters of SF media is then added to the DNA:lipid mixture. The cells are rinsed once with 5 ml of SF media, aspirated, and the DNA:lipid mixture is added. The cells are incubated at 37° C. for five hours, then 6.4 ml of DMEM/10% FBS, 1% PSN media is added to each plate. The plates are incubated at 37° C. overnight, and the DNA:lipid mixture is replaced with fresh 5% FBS/DMEM media the next day. On day 5 post-transfection, the cells are split into T-162 flasks in selection medium (DMEM+5% FBS, 1% L-Gln, 1% NaPyr, 1 μM methotrexate). Approximately 10 days post-transfection, two 150-mm culture dishes of methotrexate-resistant colonies from each transfection are trypsinized, and the cells are pooled and plated into a T-162 flask and transferred to large-scale culture.

Example 4

Expression of Zkun10 in Adenovirus

For construction of adenovirus vectors, the protein coding region of human zkun10 is amplified by PCR using primers that add PmeI and AscI restriction sites at the 5' and 3' termini respectively. Amplification is performed with a full-length zkun10 cDNA template in a PCR reaction as follows: one cycle at 95° C. for 5 minutes; followed by 15 cycles at 95° C. for 1 min., 61° C. for 1 min., and 72° C. for 1.5 min.; followed by 72° C. for 7 min.; followed by a 4° C. soak. The PCR reaction product is loaded onto a 1.2% low-melting-temperature agarose gel in TAE buffer (0.04 M Tris-acetate, 0.001 M EDTA). The zkun10 PCR product is excised from the gel and purified using a commercially available kit comprising a silica gel mambrane spin column (QIAquick® PCR Purification Kit and gel cleanup kit; Qiagen, Inc.) as per kit instructions. The PCR product is then digested with PmeI and AscI, phenol/chloroform extracted, EtOH precipitated, and rehydrated in 20 ml TE (Tris/EDTA pH 8). The zkun10 fragment is then ligated into the PmeI-AscI sites of the transgenic vector pTG12–8 and transformed into E. coli DH10B™ competent cells by electroporation. Vector pTG12–8 was derived from p2999B4 (Palmiter et al., *Mol. Cell Biol.* 13: 5266–5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The cDNA is inserted between the insulin II and hGH sequences. Clones containing zkun10 are identified by plasmid DNA miniprep followed by digestion with PmeI and AscI. A positive clone is sequenced to insure that there were no deletions or other anomalies in the construct.

DNA is prepared using a commercially available kit (Maxi Kit, Qiagen, Inc.), and the zkun10 cDNA is released from the pTG12-8 vector using PmeI and AscI enzymes. The cDNA is isolated on a 1% low melting temperature agarose gel and excised from the gel. The gel slice is melted at 70?C, and the DNA is extracted twice with an equal volume of Tris-buffered phenol, precipitated with EtOH, and resuspended in 10 ?l $H_2O$.

The zkun10 cDNA is cloned into the EcoRV-AscI sites of a modified pAdTrack-CMV (He, T-C. et al., *Proc. Natl. Acad. Sci. USA* 95:2509–2514, 1998). This construct contains the green fluorescent protein (GFP) marker gene. The CMV promoter driving GFP expression is replaced with the SV40 promoter, and the SV40 polyadenylation signal is replaced with the human growth hormone polyadenylation signal. In addition, the native polylinker is replaced with FseI, EcoRV, and AscI sites. This modified form of pAdTrack-CMV is named pZyTrack. Ligation is performed using a commercially available DNA ligation and screening kit (Fast-Link®) kit; Epicentre Technologies, Madison, Wis.). Clones containing zalpha51 are identified by digestion of mini prep DNA with FseI and AscI. In order to linearize the plasmid, approximately 5 µg of the resulting pZyTrack zkun10 plasmid is digested with PmeI. Approximately 1 µg of the linearized plasmid is cotransformed with 200 ng of supercoiled pAdEasy (He et al., ibid.) into *E. coli* BJ5183 cells (He et al., ibid.). The co-transformation is done using a Bio-Rad Gene Pulser at 2.5 kV, 200 ohms and 25 µFa. The entire co-transformation mixture is plated on 4 LB plates containing 25 µg/ml kanamycin. The smallest colonies are picked and expanded in LB/kanamycin, and recombinant adenovirus DNA is identified by standard DNA miniprep procedures. The recombinant adenovirus miniprep DNA is transformed into *E. coli* DH10B™ competent cells, and DNA is prepared using a Maxi Kit (Qiagen, Inc.) according to kit instructions.

Approximately 5 µg of recombinant adenoviral DNA is digested with PacI enzyme (New England Biolabs) for 3 hours at 37° C. in a reaction volume of 100 µl containing 20–30 U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc. Montreal, Qc. Canada), inoculated the day before and grown to 60–70% confluence, is transfected with the PacI digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy)propyl]-N,N,N-trimethyl-ammonium salts (DOTAP) (Boehringer Mannheim, Indianapolis, Ind.) is diluted to a total volume of 100 µl with HBS. The DNA is added to the DOTAP, mixed gently by pipeting up and down, and left at room temperature for 15 minutes. The media is removed from the 293A cells and washed with 5 ml serum-free minimum essential medium (MEM) alpha containing 1 mM sodium pyruvate, 0.1 mM MEM non-essential amino acids, and 25 mM HEPES buffer (reagents obtained from Life Technologies, Gaithersburg, Md.). 5 ml of serum-free MEM is added to the 293A cells and held at 37° C. The DNA/lipid mixture is added drop-wise to the T25 flask of 293A cells, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for GFP expression and formation of foci (viral plaques).

Seven days after transfection of 293A cells with the recombinant adenoviral DNA, the cells express the GFP protein and start to form foci (viral "plaques"). The crude viral lysate is collected using a cell scraper to collect all of the 293A cells. The lysate is transferred to a 50-ml conical tube. To release most of the virus particles from the cells, three freeze/thaw cycles are done in a dry ice/ethanol bath and a 37° C. waterbath.

The crude lysate is amplified (Primary (1°) amplification) to obtain a working "stock" of zkun10 rAdV lysate. Ten 10 cm plates of nearly confluent (80–90%) 293A cells are set up 20 hours previously, 200 ml of crude rAdV lysate is added to each 10-cm plate, and the cells are monitored for 48 to 72 hours for CPE (cytopathic effect) under the white light microscope and expression of GFP under the fluorescent microscope. When all of the 293A cells show CPE, this stock lysate is collected and freeze/thaw cycles performed as described above.

A secondary (2°) amplification of zkun10 rAdV is then performed. Twenty 15-cm tissue culture dishes of 293A cells are prepared so that the cells are 80–90% confluent. All but 20 ml of 5% MEM media is removed, and each dish is inoculated with 300–500 ml of the 1° amplified rAdv lysate. After 48 hours the 293A cells are lysed from virus production, the lysate is collected into 250-ml polypropylene centrifuge bottles, and the rAdV is purified.

NP-40 detergent is added to a final concentration of 0.5% to the bottles of crude lysate in order to lyse all cells. Bottles are placed on a rotating platform for 10 minutes agitating as fast as possible without the bottles falling over. The debris is pelleted by centrifugation at 20,000×G for 15 minutes. The supernatant is transferred to 250-ml polycarbonate centrifuge bottles, and 0.5 volume of 20% PEG8000/2.5 M NaCl solution is added. The bottles are shaken overnight on ice. The bottles are centrifuged at 20,000×G for 15 minutes, and the supernatant is discarded into a bleach solution. Using a sterile cell scraper, the white, virus/PEG precipitate from 2 bottles is resuspended in 2.5 ml PBS. The resulting virus solution is placed in 2-ml microcentrifuge tubes and centrifuged at 14,000×G in the microcentrifuge for 10 minutes to remove any additional cell debris. The supernatant from the 2-ml microcentrifuge tubes is transferred into a 15-ml polypropylene snapcap tube and adjusted to a density of 1.34 g/ml with CsCl. The solution is transferred to 3.2-ml, polycarbonate, thick-walled centrifuge tubes and spun at 348,000×G for 3–4 hours at 25?C. The virus forms a white band. Using wide-bore pipette tips, the virus band is collected.

A commercially available ion-exchange columns (e.g., PD-10 columns prepacked with Sephadex® G-25M; Pharmacia Biotech, Piscataway, N.J.) is used to desalt the virus preparation. The column is equilibrated with 20 ml of PBS. The virus is loaded and allowed to run into the column. 5 ml of PBS is added to the column, and fractions of 8–10 drops are collected. The optical densities of 1:50 dilutions of each fraction are determined at 260 nm on a spectrophotometer. Peak fractions are pooled, and the optical density (OD) of a 1:25 dilution is determined. OD is converted to virus concentration using the formula: (OD at 260 nm)(25)(1.1×$10^{12}$)=virions/ml.

To store the virus, glycerol is added to the purified virus to a final concentration of 15%, mixed gently but effectively, and stored in aliquots at −80?C.

A protocol developed by Quantum Biotechnologies, Inc. (Montreal, Canada) is followed to measure recombinant virus infectivity. Briefly, two 96-well tissue culture plates are seeded with 1×$10^4$ 293A cells per well in MEM containing 2% fetal bovine serum for each recombinant virus to be assayed. After 24 hours 10-fold dilutions of each virus from 1×$10^{-2}$ to 1×$10^{-14}$ are made in MEM containing 2% fetal bovine serum. 100 μl of each dilution is placed in each of 20 wells. After 5 days at 37° C., wells are read either positive or negative for CPE, and a value for "Plaque Forming Units/ml" (PFU) is calculated.

Example 5

Activity Assays

A. Trypsin Inhibitory Activity Assay on Mammalian Cell Culture Supernatants

Conditioned media from cells expressing Kunitz-type inhibitors is assayed for trypsin inhibitor activity. For each clone, 20–100 μl of conditioned medium is added to a solution containing 2.4 μg/ml trypsin (Worthington Biochemical, Freehold, N.J.) in 100 mM NaCl, 50 mM Tris (pH 7.4) to give a final volume of 300 μl. The reactions are incubated at 23° C. for 30 minutes after which 20 μl of 10 mM chromogenic substrate S-2251 (D-Val-Leu-Lys-Nan; Chromogenix, AB, Mölndal, Sweden) is added to a final concentration of 0.6 mM. The residual trypsin activity is measured by absorbance at 405 nm.

B. Activity Assay on Yeast Culture Supernatants

Trypsin inhibitory activity is measured on the spent media from cultures of yeast transformants described in Example 3 by diluting 3.2 μl of each spent medium sample with 80 μl of assay buffer (50 mM Tris HCl, pH 7.4, 100 mM NaCl, 2 mM $CaCl_2$, 0.1% w/v PEG 20,000). The diluted supernatant is added to 80 ml of 133 nM bovine trypsin (Novo Nordisk A/S, Copenhagen, DK) diluted in assay buffer, and the mixture is incubated for 10 minutes at room temperature. After incubation, 100 ml of 1.8 mM peptidyl nitroanilide substrate S2251 (D-Val-Leu-Lys-Nan; Kabi) diluted in assay buffer is added to each sample, and the samples are incubated with the substrate for 30 minutes. Trypsin inhibitory activity is indicated by a colorless solution. A control reaction, which results in a yellow solution, is produced by a supernatant from a yeast strain not expressing any Kunitz-type inhibitor.

Example 6

Purification of Kunitz-Type Inhibitors

A. Purification of Kunitz-Type Inhibitors from Transfected Mammalian Cell Culture Supernatants zkun10 is purified from conditioned medium by sequential application of heparin agarose, MONO Q, MONO S and SUPEROSE 12 chromatography as described in more detail below. Conditioned serum-free media is adjusted to pH 7.5 with 1 N NaOH and filtered through a 0.22-μm filter. A 2.6×35 cm heparin sepharose column (Pharmacia Biotech Inc., Piscataway, N.J.) is equilibrated at 4° C. with Buffer A (50 mM Tris-HCl (pH 7.5), 10% glycerol). The filtered media is applied to the equilibrated column at a flow rate of 3 ml/min. Following sample application, the column is washed with Buffer A containing 0.2 M NaCl. zkun10 activity, as judged by its ability to inhibit trypsin is eluted from the column with Buffer A containing 1 M NaCl. The eluent from the heparin sepharose column is dialyzed at 4° C. against 25 mM Tris-HCl (pH 7.5), 10% glycerol. The retentate is subjected to FPLC (Pharmacia Biotech Inc.) on a 5×50 mm column containing an anion exchanger with quaternary amine groups crosslinked to a beaded hydrophylic resin such as a MONO Q (MONO Q HR 5/5; Pharmacia Biotech Inc., Piscataway, N.J.) or the like that has been equilibrated with 25 mM Tris-HCl (pH 7.5), 10% glycerol at room temperature. zkun10 is eluted from the column in a linear NaCl gradient (from 0–0.5 M NaCl) at a flow rate of 1 ml/min. The zkun10 fractions are pooled and dialyzed against 25 mM sodium citrate (pH 5.0), 10% glycerol. The retentate is then subjected to FPLC at room temperature on a 5×50 mm column containing a cation exchanger with charged sulfonic groups coupled to a beaded hydrophylic resin such as MONO S (MONO S HR 5/5, Pharmacia Biotech Inc.) or the like at a flow rate of 0.5 ml/min. zkun10 activity is eluted from the MONO S column with a gradient elution from 25 mM sodium citrate (pH 5.0), 10% glycerol to 25 mM Tris-HCl (pH 7.5), 10% glycerol, 1 M NaCl. Fractions containing zkun10 activity are pooled and concentrated to approximately 1 ml by ultrafiltration. The concentrated samples are subjected to FPLC across a cross-linked agarose gel filtration matrix having a porosity suitable for the separation of proteins from 1×$10^3$ to 3×$10^5$ MW such as SUPEROSE 12 (Pharmacia Biotech Inc., Piscataway, N.J.) or the like at room temperature in 50 mM Tris-HCl (pH 7.5), 100 mM NaCl. Fractions eluted from the FPLC with zkun10 activity are subjected to SDS-PAGE, and pure fractions are pooled and stored at −80° C.

B. Purification of Kunitz-Type Inhibitors from Yeast Culture Supernatants

Kunitz-type inhibitors are purified from yeast culture supernatants essentially as described by Norris et al. (ibid.; which is incorporated herein by reference). Selected transformants are grown in 10 liters of YEPD for approximately 40 hours at 30° C. until an $OD_{600}$ of approximately 25 has been reached. The culture is centrifuged, and the supernatant is decanted.

For purification, a 300 ml-1000 ml aliquot of supernatant is adjusted to pH 2.3 and applied to a column holding 8 ml of S-Sepharaose (Pharmacia-LKB Biotechnology AS, Alleroed, Denmark) that has been previously equilibrated with 20 mM Bicine, pH 8.7 (Sigma Chemical Co., St. Louis, Mo.). After the column has been extensively washed with 20 mM Bicine, pH 8.7, the Kunitz-type inhibitor is eluted with 30 ml of 20 mM Bicine, pH 8.7 containing 1 M NaCl. The eluted material is desalted by application to a Sephadex G-25 column (Pharmacia-LKB Biotechnology AS, Alleroed, Denmark; 2.5×30 cm) that has been equilibrated with 20 mM $NH_4HCO_3$, pH 7.8. The Kunitz-type inhibitor is eluted with 20 mM $NH_4HCO_3$, pH 7.8.

The Kunitz-type inhibitor is further purified and concentrated by chromatography on a Mono S column (Pharmacia-LKB Biotechnology AS, Alleroed, Denmark; 0.5×5 cm) equilibrated with 20 mM Bicine, pH 8.7. After washing with the equilibration buffer at 2 ml/min for 10 minutes, gradient elution of the Kunitz-type inhibitor is carried out over twelve minutes at 1 ml/min from 0–0.6 M NaCl in the equilibration buffer. Peak samples are pooled, and the Kunitz-type inhibitor is purified using reverse phase HPLC on a Vydac 214TP510 column (Mikro-lab, Aarhus, Denmark; 1.0×25 cm) with a gradient elution at 4 ml/min from 5% A (0.1% trifluoroacetic acid (TFA) in water) to 45% B (0.7% TFA in acetonitrile) in 20 minutes. The purified product in lyophilized in water, and inhibitor activity is measured.

Kunitz inhibitor activity is measured using the method essentially described by Norris et al. (ibid.). Briefly, various fixed concentrations of the Kunitz-type inhibitor are incubated in the presence of 0.24 μg/ml of porcine trypsin (Novo Nordisk A/S, Bagsvaerd, Denmark), 12.8 CU/I human plasmin (Kabi, Stockholm, Sweden) or 0.16 nkat/ml human plasma kallikrein (Kabi) in 100 mM NaCl, 50 mM Tris HCl, pH 7.4. After a 30 minute incubation the residual enzymatic activity is measured by the cleavage of a substrate solution containing 0.6 mM of either of the chromogenic peptidyl nitroanilide trypsin/plasmin substrates S2251 (D-Val-Leu-Lys-Nan; Kabi) or S2302 (D-Pro-Phe-Arg-Nan; Kabi) in assay buffer. The samples are incubated for 30 minutes after which the absorbance of each sample is measured at 405 nm. Plasmin or trypsin activity is measured as a decrease in absorbance at 405 nm. From the results, the apparent inhibition constant Ki is calculated.

Example 7

Effect of Recombinant Zkun10 on the Amydolytic Activities of Human Thrombin, and Human Factor XA A. Thrombin Amidolytic Activity Assay The ability of recombinant zkun10 to inhibit the amidolytic activity of human thrombin is determined by a colometric assay using human thrombin (prepared as described by Pedersen, et al., *J. Biol. Chem.* 265: 16786–16793, 1990; which is incorporated by reference herein in its entirety) and various concentrations of recombinant zkun10. The assay is set up in a microtiter plate format. Reactions of 200 μl are prepared in the wells of the microtiter plate. The reaction mixtures contain various concentrations of recombinant zkun10 and 20 nM human thrombin in 50 mM Tris-HCl (pH 7.5), 0.1% BSA, 5 mM $CaCl_2$. The reactions are incubated at 37° C. for 15 minutes. Following incubation, 50 μl of 10 mM the chromogenic substrate S-2238 (H-D-Phe-Pip-Arg-p-nitroanilide, Chromogenix, AB, Mölndal, Sweden) is added to each well. The absorbance at 405 nm is determined in a kinetic microplate reader (Model UVMAX, Molecular Devices).

B. Human Factor Xa Amidolytic Assay

The ability of zkun10 to inhibit the amidolytic activity of factor Xa is determined by a colorimetric assay as described above using 20 nM human factor Xa (prepared as described by Kondo, and Kisiel, *Blood* 70, 1947–1954, 1987; which is incorporated by reference herein in its entirety) in place of the 20 nM human thrombin described above. The reactions are set up and incubated as described above replacing the human thrombin with human factor Xa. Following incubation, 50 ml of 10 mM of the chromogenic substrate S-2222 (Benzoyl-Ile-Glu-Gly-Arg-p-nitroanilide, Chromogenix, AB, Mölndal, Sweden) is added to each well. The absorbance at 405 nm is determined in a kinetic microplate reader (Model UVMAX, Molecular Devices).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polypeptide comprising a sequence of amino acid residues as shown in SEQ ID NO: 2 from residue 57 (Cys) to residue 107 (Cys), wherein said polypeptide has Kunitz proteinase inhibitory activity.

2. An isolated polypeptide comprising a sequence of amino acid residues with at least 95% sequence identity to the amino acid sequence of SEQ ID NO: 2 from residue 1 (Ile) to residue 111 (Gln), wherein said polypeptide has Kunitz proteinase inhibitory activity.

3. The polypeptide of claim 2, wherein any variation in the polypeptide in the region of amino acid residues 57 to 107 is subject to the limitations as shown in SEQ ID NO: 4.

4. An isolated polypeptide comprising a sequence of amino acid residues with at least 95% sequence identity to the amino acid sequence of SEQ ID NO: 6 from residue 1

(Met) to residue 415 (Gln), wherein said polypeptide has Kunitz proteinase inhibitory activity.

5. The polypeptide of claim 4, wherein any variation in the polypeptide in the region of amino acid residues 361 (Cys) to 411 (Cys) is subject to the limitations as shown in SEQ ID NO: 4.

6. An isolated polypeptide comprising a sequence of amino acid residues as shown in SEQ ID NO: 6 from amino acid residue 1 (Met) to residue 415 (Gln), wherein said polypeptide has Kunitz proteinase inhibitory activity.

7. A fusion protein comprising at least two polypeptides, wherein a first polypeptide and second polypeptide, and wherein at least one of the polypeptides comprise a sequence of amino acid residues as shown in SEQ ID NO: 2 from amino acid residue 57 (Cys) to amino acid residue 107 (Cys).

8. A fusion protein comprising at least three polypeptides, wherein a first polypeptide comprises a secretory signal polypeptide followed by a second polypeptide comprising a collagen domain polypeptide containing one or more von Willebrand domains, followed by third polypeptide comprising one or more Kunitz domains, and wherein at least one of the Kunitz domains comprise a sequence of amino acid residues as shown in SEQ ID NO: 2 from amino acid residue 57 (Cys) to amino acid residue 107 (Cys).

9. The fusion protein of claim 8, wherein the collagen domain further comprises at least one globular domains.

10. A method of inhibiting protease degradation or activity in a composition containing plasma proteins and proteases comprising adding a zkun10 polypeptide composition comprising a sequence of amino acid residues as shown in SEQ ID NO: 2 from amino acid residue 57 to amino acid residue 107 to the composition containing plasma proteins and protease in an amount sufficient to reduce degradation of the composition by proteases or protease activity in the composition.

11. The method of claim 10, wherein the reduction of degradation or activity is determined by chromogenic substrate assays or clotting time assays.

* * * * *